(12) United States Patent
Ii et al.

(10) Patent No.: US 10,278,926 B2
(45) Date of Patent: May 7, 2019

(54) STATIN-ENCAPSULATED NANOPARTICLE PREPARATION FOR ENHANCING STEM CELL FUNCTION, STEM CELL WITH ENHANCED FUNCTION CONTAINING STATIN-ENCAPSULATED NANOPARTICLE, AND METHOD FOR PRODUCING SAME

(71) Applicants: FOUNDATION FOR BIOMEDICAL RESEARCH AND INNOVATION AT KOBE, Hyogo (JP); OSAKA MEDICAL COLLEGE, Kyoto (JP); Masaaki Ii; Yasuhiko Tabata

(72) Inventors: Masaaki Ii, Osaka (JP); Yasuhiko Tabata, Kyoto (JP)

(73) Assignee: FOUNDATION FOR BIOMEDICAL RESEARCH AND INNOVATION AT KOBE, Kobe-Shi, Hyogo (JP)

( * ) Notice: Subject to any disclaimer, the term of this patent is extended or adjusted under 35 U.S.C. 154(b) by 0 days.

(21) Appl. No.: 15/525,281

(22) PCT Filed: Nov. 11, 2015

(86) PCT No.: PCT/JP2015/081329
§ 371 (c)(1),
(2) Date: May 8, 2017

(87) PCT Pub. No.: WO2016/076227
PCT Pub. Date: May 19, 2016

(65) Prior Publication Data
US 2017/0319504 A1    Nov. 9, 2017

(30) Foreign Application Priority Data
Nov. 10, 2014 (JP) .................. 2014-228409

(51) Int. Cl.
| | |
|---|---|
| A61K 9/51 | (2006.01) |
| A61K 45/00 | (2006.01) |
| A61K 47/34 | (2017.01) |
| A61K 9/16 | (2006.01) |
| A61K 31/366 | (2006.01) |
| A61K 35/12 | (2015.01) |
| A61K 47/69 | (2017.01) |
| A61K 9/14 | (2006.01) |
| A61K 35/34 | (2015.01) |
| A61K 39/00 | (2006.01) |

(52) U.S. Cl.
CPC ............... *A61K 9/51* (2013.01); *A61K 9/141* (2013.01); *A61K 9/16* (2013.01); *A61K 31/366* (2013.01); *A61K 35/12* (2013.01); *A61K 35/34* (2013.01); *A61K 45/00* (2013.01); *A61K 47/34* (2013.01); *A61K 47/6931* (2017.08); *A61K 2039/55555* (2013.01)

(58) Field of Classification Search
CPC .................. A61K 9/51; A61K 35/12
See application file for complete search history.

(56) References Cited

U.S. PATENT DOCUMENTS

| | | | | |
|---|---|---|---|---|
| 2005/0238666 A1* | 10/2005 | Williams | ............. | A61K 31/225 424/239.1 |
| 2006/0182724 A1 | 8/2006 | Riordan | | |
| 2010/0086602 A1 | 4/2010 | Egashira | | |
| 2010/0086615 A1* | 4/2010 | Egashira | ............. | A61K 9/0078 424/501 |

FOREIGN PATENT DOCUMENTS

JP    2012-021002 A    2/2012

OTHER PUBLICATIONS

Rosuvastatin enhances the therapeutic efficacy of adipose-derived mesenchymal stem cells for myocardial infarction via PI3K/Akt and MEK/ERK pathways, Zhang et al., Basic Res Cardiol, 2013, 1-18.*
Ii M., et al., Synergistic effect of adipose-derived stem cell therapy and bone marrow progenitor recruitment in ischemic heart, Laboratory Investigation, vol. 91, pp. 539-552, 2011.
Wang C-Z., et al., Synthesis and characterization of cationic polymeric nanoparticles as simvastatin carriers for enhancing the osteogenesis of bone marrow mesenchymal stem cells, J. Colloid. Interface Sci., vol. 432, pp. 190-199, Oct. 15, 2014.
Zhang Z., et al., In Vivo Molecular Imaging of Rosuvastatin on Adipose-derived Stem Cells' Survival in post-Infarcted Mice Hearts: Role of PI3K-Akt pathway, Molecular Imaging and Biology, vol. 14, Suppl. 1, pp. S918, Presentation No.—T156, 2011.
Cai A., et al., Atorvastatin Treatment of Rats with Ischemia-Reperfusion Injury Improves Adipose-Derived Mesenchymal Stem Cell Migration and Survival via the SDF-I a/CXCR-4 Axis, Plos One, vol. 8, No. 12, pp. e79100, 2013.
International Search Report, dated Jan. 12, 2016, in International Application No. PCT/JP2015/081329.
Extended European Search Reported, dated Jul. 17, 2018, in European Patent Application No. 15892064.5.
Yokoyama, R. et al., Abstract 12139: Unique Therapeutic Effect of Statin Nanoparticle-Loaded Adipose-Derived Stem Cells on Myocardial Infarction, Circulation, vol. 130, Issue Suppl. 2, 4 pages, 2014.

* cited by examiner

*Primary Examiner* — Kyle A Purdy
(74) *Attorney, Agent, or Firm* — Knobbe, Martens, Olson & Bear, LLP

(57) ABSTRACT

A preparation containing a statin-encapsulated nanoparticle obtained by encapsulating statin in a nanoparticle containing a bioabsorbable polymer is disclosed. The nanoparticle has a number average particle diameter of less than 1000 nm. The preparation is used to enhance the function of a stem cell. A stem cell with an enhanced function is disclosed. The stem cell takes up and contains the statin-encapsulated nanoparticle.

9 Claims, 18 Drawing Sheets
Specification includes a Sequence Listing.

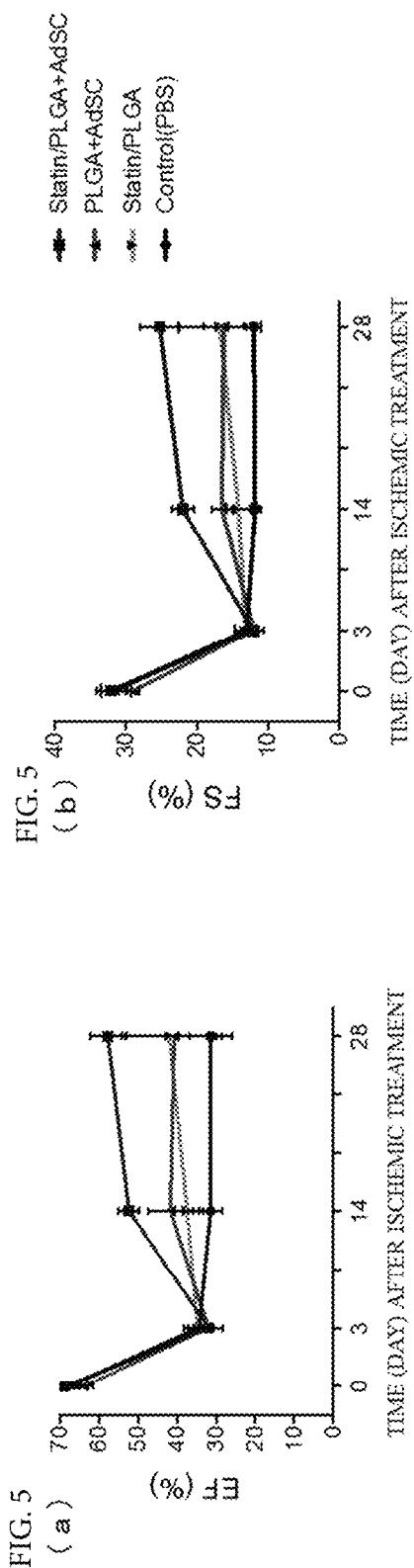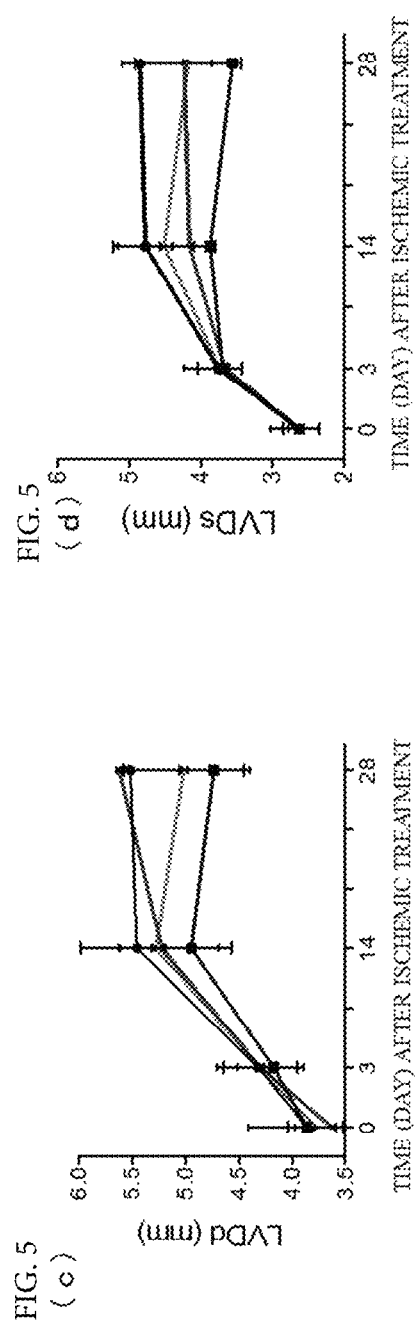
FIG. 5 (a)
FIG. 5 (b)
FIG. 5 (c)
FIG. 5 (d)

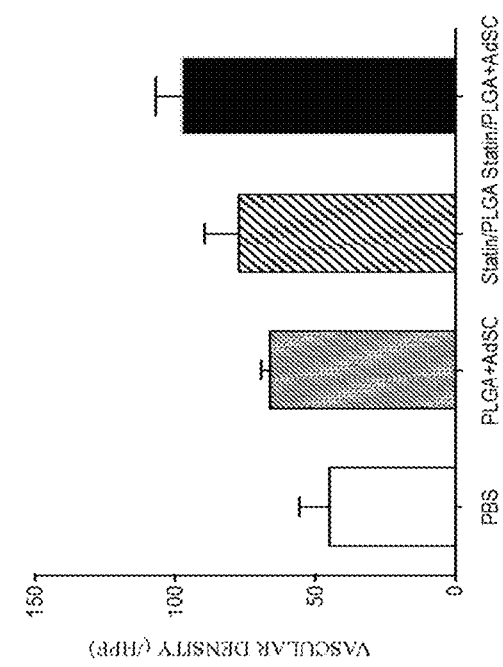
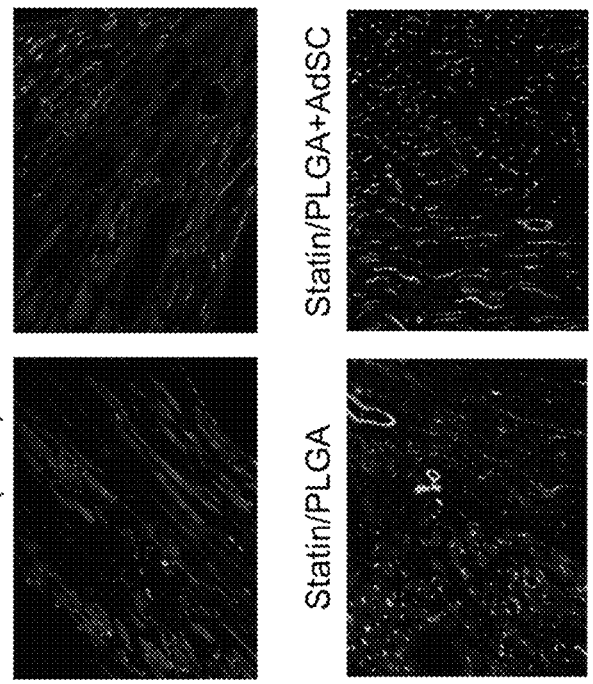
FIG. 11

STATIN-ENCAPSULATED NANOPARTICLE PREPARATION FOR ENHANCING STEM CELL FUNCTION, STEM CELL WITH ENHANCED FUNCTION CONTAINING STATIN-ENCAPSULATED NANOPARTICLE, AND METHOD FOR PRODUCING SAME

CROSS REFERENCE TO RELATED APPLICATIONS

This application is the U.S. National Stage Application under 35 U.S.C. § 371 of International Application No. PCT/JP2015/081329, filed Nov. 6, 2015, designating the U.S. and published as WO 2016/076227 A1 on May 19, 2016, which claims the benefit of Japanese Patent Application No. JP 2014-228409, filed Nov. 10, 2014. Any and all applications for which a foreign or a domestic priority is claimed is/are identified in the Application Data Sheet filed herewith and is/are hereby incorporated by reference in their entirety under 37 C.F.R. § 1.57.

SEQUENCE LISTING IN ELECTRONIC FORMAT

The present application is being filed along with an Electronic Sequence Listing as an ASCII text file via EFS-Web. The Electronic Sequence Listing is provided as a file entitled CPJ005001APCSEQLIST.txt, created and last saved on Jul. 28, 2017, which is 1,584 bytes in size. The information in the Electronic Sequence Listing is incorporated herein by reference in its entirety in accordance with 35 U.S.C. § 1.52(e).

TECHNICAL FIELD

The present invention relates to statin-included nanoparticles and specifically, to a statin-included nanoparticle preparation for enhancing the function of a cell. Moreover, the present invention relates to a stem cell comprising a statin-included nanoparticle and a method for producing the stem cell.

BACKGROUND ART

Statin is known as a compound which inhibits HMG-CoA reductase which is a rate-limiting enzyme of cholesterol biosynthesis in the liver. Statin can reduce the cholesterol level in blood and is thus used in therapeutic drugs for hypercholesterolemia. Moreover, clinical tests have revealed that statin is also effective to ischemic heart diseases such as angina pectoris and myocardial infarction and diseases such as arteriosclerosis due to the anti-inflammatory activity of the statin in addition to hypercholesterolemia.

Various studies have been conducted to improve the therapeutic effect of statin on the above-described diseases and to reduce side effects caused by the statin. For example, Patent Literature 1 discloses that statin is included in a nanoparticle, and the statin-included nanoparticle is locally applied to a patient, thereby enabling acceleration of neovascularization with a fewer amount of statin than before.

Moreover, in recent years, studies of treating ischemic heart diseases with a stem cell having multipotency and being capable of differentiating into a myocardial cell have been conducted. Non-Patent Literature 1 discloses that direct administration of adipose tissue-derived stem cells to the cardiac muscle of a myocardial infarction model mouse improved the function of the heart of the mouse and reduced the size of an infraction of the mouse.

CITATION LIST

Patent Literature

[Patent Literature 1] Japanese Unexamined Patent Application Publication No. 2012-21002

Non-Patent Literature

[Non-Patent Literature 1] Masaaki Ii et al., Laboratory Investigation (2011) 91, 539-552

SUMMARY

When, for example, a statin-included nanoparticle as described in the Patent Literature 1 is administered in order to treat ischemic heart diseases such as a myocardial infarction, statin exhibits effectiveness with smaller amount than before by locally applying the statin-included nanoparticle to a patient as described above. However, local administration to a diseased part is required, and thus the administration is not simple and requires further improvement in the effectiveness. Moreover, when intravenous administration or the like is used without using local administration, a larger dosage is required, and a side effect may be caused.

Meanwhile, as disclosed in Non-Patent Literature 1, also when ischemic heart diseases such as a myocardial infarction are treated with a stem cell, the stem cell has to be locally administered to a diseased part, and for example, when the stem cell is administered to the cardiac muscle of a mouse, an amount of $5 \times 10^5$ cells/mouse is required in order to achieve a therapeutic effect. As the stem cell, for example, a mesenchymal-derived somatic stem cell can be used. Such a stem cell can be obtained from bone marrow or adipose tissues, but the amount of the stem cell which can be obtained once is limited. Thus, when the stem cell is used in, for example, the above-described therapy, the number of cells used is preferably small. As described above, in order to obtain excellent therapeutic effects from a smaller number of stem cells, various types of functions of the stem cell have to be enhanced.

In view of the above problems, it is an object of the present invention to enable improvement in the function of a stem cell used as a cell preparation so as to improve the therapeutic effect of the stem cell on a disease while reducing side effects.

To achieve the object, the present inventors have conducted intensive studies. As a result, the present inventors found that a statin-included nanoparticle obtained by including statin to a nanoparticle is comprised in stem cell to enhance the function of the stem cell, the statin can be efficiently delivered to a desired diseased part, and a high effectiveness of treatment of various diseases such as an ischemic heart disease is shown, and the inventors completed the present invention. That is, a statin-included nanoparticle preparation according to the present invention is a preparation containing a statin-included nanoparticle obtained by including statin in a nanoparticle containing a bioabsorbable polymer, wherein the nanoparticle has a number average particle diameter of less than 1000 nm, and the statin-included nanoparticle preparation has features of being used to enhance a function of a stem cell.

Treating a stem cell with the statin-included nanoparticle preparation according to the present invention enables enhancement of the function of the treated stem cell, and administering the treated stem cell into a living body produces various types of effectiveness. Specifically, when stem cells are treated with statin-included nanoparticles preparation according to the present invention, the treated stem cells take up statin-included nanoparticles through phagocytosis, and the stem cells, which have taken up the statin-included nanoparticles, are enhanced in the migratory capacity, the proliferation capacity, and the productivity of a neovascularization factor. Thus, when stem cells treated with statin-included nanoparticles according to the present invention and being capable of differentiate into a cardiovascular system cell are administered into the body of a patient suffering from, for example, an ischemic heart disease, the stem cells accumulate and proliferate at an ischemic part, and release neovascularization factors to promote neovascularization of the ischemic part. Moreover, the accumulated and proliferating stem cells differentiate into cardiac muscle to promote regeneration of the cardiac muscle. Moreover, administering the stem cells which have taken up the statin-included nanoparticles according to the present invention promote division and proliferation of cells located near epicardium at a myocardial infarction part, thereby promoting regeneration of the cardiac muscle. Consequently, excellent therapeutic effects on the ischemic heart diseases are exhibited. Moreover, the stem cells are capable of gradually releasing statin which the stem cells have taken up, which offers various effects, such as neovascularization effects of the statin itself, which are typical of the statin. Thus, the stem cells are useful for the treatment of various diseases such as an ischemic heart disease. Moreover, statin released from the stem cells accumulated at a diseased part can facilitate accumulation of stem cells and bone marrow-derived endothelial progenitor cells (EPCs) in a body. As a result, for example, in the case of the ischemic heart disease, regeneration of the cardiac muscle at an ischemic part can be further promoted. When a compound such as statin is simply intravenously administered, the compound is transported to a diseased part along with a bloodstream, but in the case of the ischemic heart disease such as a myocardial infarction, the bloodstream is inhibited, and therefore, it is difficult to normally transport the compound to the diseased part. However, in the case of the present invention, statin is incorporated into and transported by stem cells having an enhanced migratory property, and therefore, the compound can arrive at the diseased part even when the bloodstream is inhibited. That is, a good drug delivery system can be obtained, thereby enabling a reduction in the number of cells to be administered. The actions described above achieve extremely high effect for the treatment of ischemic heart diseases such as a myocardial infarction. Note that the number average particle diameter of the nanoparticle is less than 1000 nm so that the stem cells efficiently take up statin-included nanoparticles through the phagocytosis.

In the statin-included nanoparticle preparation according to the present invention, poly lactic acid (PLA) or poly(lactic co-glycolic acid (PLGA) may be used as the bioabsorbable polymer.

Hydrolysis of the PLA and the PLGA in a body enables included statin to be released. Moreover, the hydrolysis of the PLA decomposes the PLA into lactic acid, and the hydrolysis of the PLGA decomposes the PLGA into lactic acid and glycol, which are eventually decomposed into water and carbon dioxide gas respectively. Therefore, the PLA or the PLGA is very preferably used as a nanoparticle material, because the PLA and the PLGA are harmless to animal such as human.

The statin-included nanoparticle preparation according to the present invention is preferably a preparation for enhancing adipose-derived stem cells as the stem cells.

To obtain the adipose-derived stem cells, adipose tissues are collected, the collected tissues are subjected to collagenase treatment, and then, only mononuclear leukocyte cells are collected by a centrifugal specific gravity method, the collected mononuclear leukocyte cells are incubated for about 4 days in an incubation plate, and bonded cells can be selected and separated as the adipose-derived stem cells. Moreover, a large quantity of adipose-derived stem cells can be easily extracted, separated, and incubated from adipose tissues by using Celution system (manufactured by Cytori Therapeutics, Inc.) or the like. The adipose-derived stem cells belong to mesenchymal stem cells, have excellent multipotency, can be easily collected at a large quantity as described above, and are thus advantageously used for treatment of various types of diseases.

Moreover, a stem cell with an enhanced function according to the present invention has features of containing statin-included nanoparticles obtained by including the statin in biocompatibility nanoparticles.

The stem cell with an enhanced function according to the present invention contains the statin-included nanoparticles, and therefore, as described above, cell functions are enhanced by the statin-included nanoparticles, and the stem cells can exhibit excellent effect for treatment of various diseases including an ischemic heart disease. Moreover, the cell with an enhanced function according to the present invention can gradually release statin, and the gradually released statin can facilitate accumulation of bone marrow stem cells and bone marrow-derived endothelial progenitor cells (EPCs), and therefore, the cell is advantageous for treatment of ischemic heart diseases or the like.

For the reasons described above, the stem cell with an enhanced function according to the present invention is preferably the adipose-derived stem cell, and is preferably a stem cell administered to patients to treat ischemic heart diseases such as a myocardial infarction.

Moreover, the stem cell with an enhanced function according to the present invention may be in preparation form as a cell preparation obtained by mixing the stem cell with a pharmaceutically acceptable solvent and a vehicle. The stem cell according to the present invention is preferably administered to a living body without requiring an operation such as thoracotomy, and is preferably in preparation form as a cell preparation for intravenous administration. In this way, the stem cell according to the present invention can be easily administered to patients. Moreover, as described above, the stem cell with an enhanced function according to the present invention functions as an excellent drug delivery system and can gradually release statin while enabling accumulation of the stem cell on a desired diseased part. Thus, the stem cell does not have to be locally administered but can provide high effectiveness with a small amount even when intravenous administration is adopted.

A method for producing a stem cell with an enhanced function according to the present invention includes a step of treating stem cells with the statin-included nanoparticles. In particular, in the step of treating the stem cells with the statin-included nanoparticles, the statin-included nanoparticles are preferably added to achieve a concentration of 20 µg/mL to 100 µg/mL in a medium for incubation or the stem cells, and a treatment time period for this step is preferably 30 minutes to 2 hours.

In this way, a simple step of adding the statin-included nanoparticles to the incubation medium for incubation of the stem cells enables a production of the stem cells with an enhanced function as described above. Moreover, the treatment at the concentration and with the time period as described above enables the stem cells to efficiently take up the statin-included nanoparticles.

In the method for producing the stem cell with an enhanced function according to the present invention, an adipose-derived stem cell is preferably used as the stem cell for the reason as described above, and a stem cell for treatment of ischemic heart diseases is preferably used.

According to a statin-included nanoparticle according to the present invention, a stem cell with an enhanced function containing the statin-included nanoparticle, and a method for producing the stem cell, the function of the stem cell can be enhanced, and administration of the stem cell to a living body produces effects for various diseases such as an ischemic heart disease.

BRIEF DESCRIPTION OF THE DRAWINGS

FIG. 4(a) to FIG. 4(c) are graphs illustrating measurement results of mRNA expression of a neovascularization factor in the adipose-derived stem cells treated with the statin-included nanoparticles by a quantitative PCR method, wherein FIG. 4(a) shows a measurement results of RNA expression of VEGF-A as the neovascularization factor, FIG. 4(b) shows a measurement results of RNA expression of VEGF-C as the neovascularization factor, and FIG. 4(c) shows a measurement results of RNA expression of FGF-2 as the neovascularization factor.

FIG. 5(a) to FIG. 5(d) are graphs illustrating results of medical ultrasound of hearts of myocardial infarction model mice in respective groups administered with PBS, statin-included nanoparticles, adipose-derived stem cells, or adipose-derived stem cells which have taken up statin-included nanoparticles, wherein FIG. 5(a) shows the left ventricular ejection fraction (EF), FIG. 5(b) shows the left ventricular fractional shortening (FS), FIG. 5(c) shows the left ventricular end-diastolic dimension (LVDd), and FIG. 5(d) shows the left ventricular end-systolic dimension (LVDs).

FIG. 11(a) and FIG. 11(b) show measurement results of the vascular density in cut pieces of infract parts of the heart of the myocardial infarction model mice administered with PBS, statin-included nanoparticles, adipose-derived stem cells which have taken up statin-non-included nanoparticles, or adipose-derived stem cells which have taken up statin-included nanoparticles, the pieces being stained with isolectin B4, wherein FIG. 11(a) shows microphotographs of the stained pieces, and FIG. 11(b) is a graph illustrating the measured vascular density.

DETAILED DESCRIPTION

Figure 1:
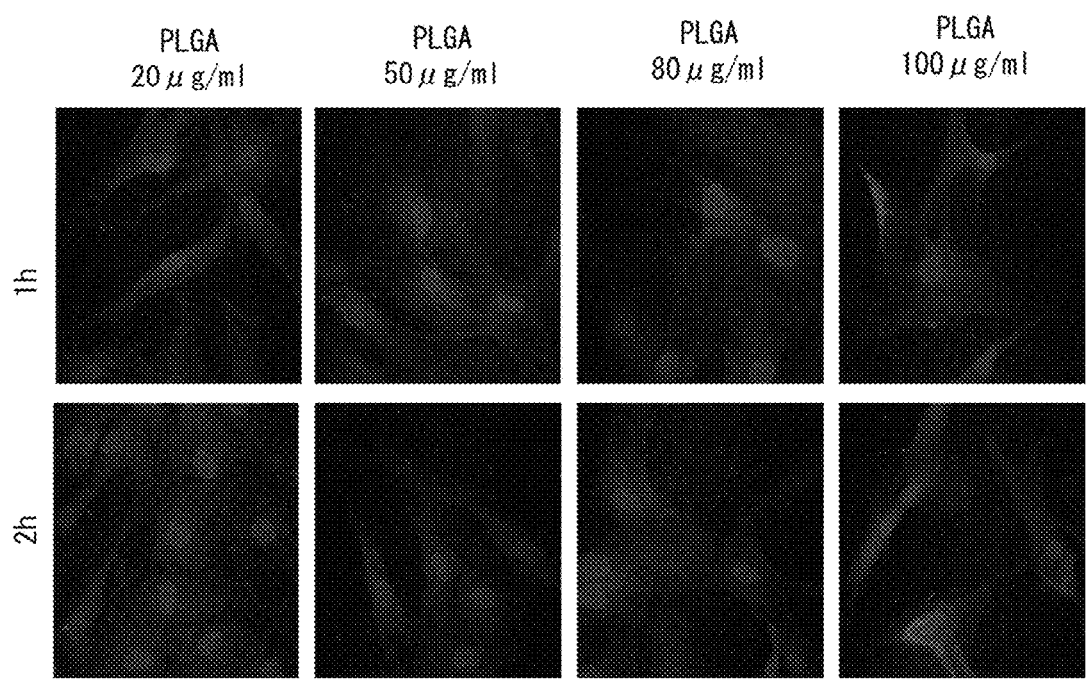
FIG. 1 shows photographs of adipose-derived stem cells in incubation media observed by a confocal laser fluorescence microscope, the adipose-derived stem cells being observed one hour and two hours after addition of rhodamine red fluorescent dye-included PLA nanoparticles to the incubation media so as to achieve a final concentration of 20 μg/mL, 50 μg/mL, 80 μg/mL, and 100 μg/mL.

Embodiments of the present invention will be described below with reference to the drawings. The following description of preferable embodiments is substantially mere examples and does not intend to limit the present invention, application method or application thereof.

Statin-included nanoparticles used for a statin-included nanoparticle preparation according to the present invention are statin-included nanoparticles which are obtained by including statin in nanoparticles containing a polylactic acid-glycolic acid copolymer and are used to enhance the function of a stem cell. The statin-included nanoparticle preparation according to the present invention may contain an additive, such as a stabilizing agent, a preservative, a buffer agent, a pH adjustor, and a vehicle generally used for preparation in addition to the statin-included nanoparticles.

In the present invention, statin includes all compounds which are 3-hydroxy-3-methylglutaryl-coenzyme A (HMG-CoA) reductase inhibitors. Examples of the statin include simvastatin, rosuvastatin, pitavastatin, atorvastatin, cerivastatin, fluvastatin, pravastatin, lovastatin, and mevastatin. As described above, it is known that statin has a cholesterol-lowering effect. Additionally, extensive clinical tests have revealed that statin reduces the risk of the occurrence or development of a cardiovascular event. Moreover, there have been a large number of reports about a neovascularization promoting activity via vascular endothelial cells and bone marrow-derived endothelial progenitor cells.

In the present embodiment, the material of the nanoparticle is not limited as long as statin can be included in the nanoparticle, but a nanoparticle containing poly lactic acid (PLA) or poly(lactic co-glycolic acid) (PLGA) is preferably used. The PLA is hydrolyzed in vivo and is decomposed into lactic acid, and the PLGA is hydrolyzed in vivo and is decomposed into lactic acid and glycol, which eventually become water and carbon dioxide gas, respectively. Thus, the PLA and the PLGA are thus harmless in vivo, and are preferable.

In the present invention, the statin-included nanoparticle can be produced by any method as long as the method can process the statin-included nanoparticle to have less than 1000 nm, preferably about 100 nm to 400 nm, more preferably 200 nm to 400 nm when measured by a light scattering method from the viewpoint of the in-take efficiency of the stem cell, but the statin-included nanoparticle is preferably produced by using a spherical crystallization technique. The spherical crystallization technique is known as a method designing a spherical crystal grain by controlling crystal formation•growth process in the final process of a compound synthesis to enable processing of the spherical crystal grain by directly controlling its physical property. One of the spherical crystallization techniques is a known emulsion solvent diffusion method (ESD method).

The emulsion solvent diffusion method is performed by using two organic solvents, a good solvent in which a bioabsorbable polymer such as the PLA or the PLGA for inclusion of statin is soluble and a poor solvent in which the polymer is insoluble. First, a polymer such as the PLA or the PLGA is dissolved in the good solvent, and a statin solution is added and mixed with the good solvent without causing precipitation of the polymer, thereby obtaining a mixture. When the mixture is dropped in the poor solvent which is agitated, a rapid mutual diffusion of the good solvent into the poor solvent and the poor solvent into the good solvent occurs, which disturbs the interface between an organic solvent phase and an aqueous phase. Thus, the good solvent self-emulsifies, and emulsion drops each having a submicron size are formed. Then, the mutual distribution of the good solvent and the poor solvent further advances, and solubilities of the polymer such as the PLA or the PLGA and the statin in the emulsion drops decrease. As a result, polymer nanoparticles of a spherical crystal grains containing statin are generated.

In the present invention, the stem cell is a cell having totipotency, multipotency, or pluripotency. Examples of the stem cell include somatic stem cells such as embryonic stem cells (ES cells), induced pluripotent stem cells (iPS cells), and mesenchymal stem cells. In the present invention, in order to obtain a large number of stem cells more easily and in larger quantity, a mesenchymal stem cell obtained from a bone marrow tissue, an adipose tissue, or the like is preferably used. Among them, an adipose-derived stem cell is particularly preferably used. Administration of the adipose-derived stem cell alone has already been clinically performed, and it is known that the adipose-derived stem cell differentiates into adipose, bones, a liver, a heart, et al. The adipose-derived stem cell can be obtained from an adipose tissue, and the adipose tissue can be easily obtained from, for example, subcutaneous adipose by a minimally invasive technique such as fat sucking. The adipose-derived stem cell can be abundantly collected by being extracted and separated from the thus obtained adipose tissues by using Celution system (manufactured by Cytori Therapeutics Inc.) or the like. Thus, the adipose-derived stem cell is particularly advantageously used as the stem cell according to the present invention.

Treatment of stem cells with the statin-included nanoparticles according to the present invention is performed by adding to, for example, an incubation medium in which the stem cells are incubated. In this way, the statin-included nanoparticles are incorporated into the stem cells through phagocytosis, and therefore, the stem cells can easily contain the statin-included nanoparticles without using a particular reagent, et al.

The stem cells treated with the statin-included nanoparticles according to the present invention are enhanced in the migratory capacity, the proliferation capacity, and the productivity of a neovascularization factor, and the therapeutic effect on ischemic heart diseases such as, in particular, a myocardial infarction. Specifically, when the adipose-derived stem cells treated with the statin-included nanoparticles according to the present invention are intravenously administered to a patient suffering from an ischemic heart disease, the adipose-derived stem cells reach the heart via a bloodstream and their migratory property due to the enhanced migratory property and proliferation characteristic, accumulate and proliferate at an ischemic injury cardiac muscle part, and differentiate into a cardiovascular system cells. Moreover, the statin-included nanoparticles containing adipose-derived stem cells which have accumulated are promoted to produce and release neovascularization factors, and many neovascularization factors promote regeneration of cardiac muscle tissues.

Moreover, as described above, the adipose-derived stem cells hydrolyze the statin-included nanoparticles taken up in the cells to gradually release the included statin. Thus, when the adipose-derived stem cells are administered to patients, the adipose-derived stem cells gradually release the statin in the ischemic injury cardiac muscle after the administration, and the released statin promotes accumulation of bone marrow stem cells and/or bone marrow-derived endothelial progenitor cells (EPCs), promotes differentiation of the bone marrow stem cells into cardiovascular system cells, and promotes regeneration of tissues. It is know that each EPC is one cell fractionation of blood corpuscle hematopoietic stem cells which are present in the bone marrow, the EPCs are present in peripheral circulation blood, though small in quantity, and the EPCs differentiate into endothelial cells which accumulate at ischemic tissues and form capillary vessels to be useful for formation of a newborn blood vessel. Clinical tests of the EPCs as a cell treatment source for neovascularization for ischemic diseases have been widely performed and such clinical tests are ongoing. Moreover, it is also reported that the EPCs differentiates not only into a vascular endothelial cell but also into a myocardial cell. The stem cells containing the statin-included nanoparticles of the present invention can accumulate the EPCs having such functions at an ischemic injury cardiac muscle part and are thus very effective for treatment of the ischemic injury cardiac muscle part. Moreover, administration of the stem cells containing the statin-included nanoparticles of the present invention causes proliferation of cells located in the vicinity of epicardium of a myocardial infarction part while newly causing granulation to promote cardiac muscle. As a result, advantages for treatment of the myocardial infarction are obtained. Note that the stem cells containing the statin-included nanoparticles of the present invention can provide effects not only for the treatment of the ischemic heart diseases but also for the treatment of injuries of organs other than the heart where the stem cells can differentiate due to the effect of statin and/or regeneration functions of the stem cells and the EPCs.

EXAMPLES

Examples are shown below to describe a statin-included nanoparticle preparation for enhancing a stem cell function, a stem cell with an enhanced function containing a statin-included nanoparticle, and a method for producing the stem cell according to the present invention in detail.

First, a method for manufacturing the statin-included nanoparticle will be described. Here, in particular, simvastatin was used as the statin, and a nanoparticle containing a polylactic acid polymer (PLA) was used as the nanoparticle.

In a mixed solution of 2 mL acetone and 0.5 mL ethanol, 50 mg PLA (Wako Pure Chemical Industries, Ltd., PLA0020, mean weight molecular weight 20000) and 2.5 mg simvastatin were dissolved to obtain a polymer solution. The polymer solution was dropped in 10 mL 2-wt %-PVA solution agitated at 500 rpm at a room temperature to obtain a simvastatin-included PLA nanoparticle suspension. Subsequently, while the agitation at 500 rpm was continued at a room temperature, organic solvents (acetone and ethanol) were removed by evaporation. After the removal of the solvents by evaporation for about 5 hours, the suspension was subjected to centrifugal separation performed at 4° C. and at 60000 g for about 30 minutes to collect sediments, and resuspension of the sediments in distilled water was performed. The centrifugal separation and the resuspension in the distilled water were performed three times in total. Then, the suspension was freeze-dried for one night to obtain simvastatin-included PLA nanoparticles. In 1 mg nanoparticles, 24.94 μg simvastatin were included. In the following test, the simvastatin-included PLA nanoparticles were used.

Next, the following test was performed in order to study the optimal treatment concentration for treatment of stem cells with the thus obtained statin-included nanoparticles.

In order to conduct the test, first, Adipose derived Stem Cell (AdSC) is obtained from a human adipose tissue by a known method using collagenase treatment and a centrifugal specific gravity method. The details of the method will be described below. First, a collagenase 1-type (1 mg/mL, Wako 035-17604)/1% BSA HBSS solution containing DNase I (0.1 mg/mL, Roche, 1284932) and 3 mM $CaCl_2$ was prepared as a collagenase solution. Then, a human adipose tissue (about 1 g to 2 g) was cut into fine pieces with a knife. The pieces were put in a 15-mL tube together with the collagenase solution having a volume three times the volume of the tissue and were subjected to shaking incubation at 37° C. for 60 minutes. Thereafter, in the 15-mL tube after the incubation, 5 mM EDTA/PBS (produced by diluting EDTA (0.5M EDTA, pH 8.0, Life Technologies, AM9260G), 10×DPBS, Ca(−), Mg(−) (GIBCO, 14200-166)) at a room temperature was added to obtain a cell suspension of about 15 mL, and centrifugation at 300 g×5 min was performed, and then, supernatant (containing a adipose layer) was removed by sucking, and 5 mM EDTA/PBS was added to obtain a cell suspension of 20 mL. The obtained cell suspension was collected into a new 50-mL tube through a cell strainer (70 μm, BD), and each 10 mL of the collected cell solution was gently superposed in a corresponding one two 15-mL tubes containing 4 mL Histopaque 1077 at a room temperature without mixing. Centrifugation of these tubes were performed at a room temperature and at 800 g×20 min (breakless), and after the centrifugation, only a mononuclear leukocyte cell layer was collected with a 2.5-mL syringe with a 18-G needle, was transferred into a new 15-mL tube, and cooled 5 mM EDTA/PBS was added to obtain a solution of 14 mL. Then, centrifugation at 200 g×10 min (with a break) was performed, and supernatant was abandoned. Then, 1 mL cooled 5 mM EDTA/PBS suspended and diluted the cell to obtain a suspension of 14 mL, and then centrifugation at 200 g×10 min was performed, and supernatant was abandoned. A cell pellet which had been obtained was suspended in a primary incubation medium (10% FBS/DMEM F12, Sigma D8042+ Antibiotic-Antimycotic, GIBCO 15240-062) and was then seeded on an incubation plate at a cell density of about $3×10^4$ cells/$cm^2$ to $4×10^4$ cells/$cm^2$. Then, the cell pellet was incubated in a 5%-$CO_2$ incubator for 4 to 5 days, and adherent cells were used as human-cell-derived stem cells in experiments.

After the human-cell-derived stem cells were thus obtained, rhodamine red fluorescent dye-included PLA nanoparticles obtained by including a rhodamine red fluorescent dye, instead of statin, in PLA nanoparticles by the emulsion solvent diffusion method were added to the incubation media of the adipose-derived stem cells so as to achieve a final concentration of 20 μg/mL, 50 μg/mL, 80 μg/mL, or 100 μg/mL. One hour (1 h) or two hours (2 h) after the addition, inclusion of the rhodamine red fluorescent dye-included PLA nanoparticles was observed with a confocal laser fluorescence microscope. Note that nuclei were dyed with DAPI by a general method. The results of the study are shown in FIG. 1.

As shown in FIG. 1, it can be seen that the rhodamine red fluorescent dye-included PLA nanoparticles were incorporated into the adipose-derived stem cells at all the concentrations. Note that the amount of the rhodamine red fluorescent dye-included PLA nanoparticles incorporated into the adipose-derived stem cells increases in a treatment-concentration-dependent manner. Moreover, it can also be seen that the amount of the simvastatin-included PLA nanoparticles incorporated into the adipose-derived stem cells is larger in the case where the treatment time period was one hour than in the case where the treatment time period was two hours. In particular, it was confirmed that when the adipose-derived stem cells were treated with the rhodamine red fluorescent dye-included PLA nanoparticles at a concentration of 100 µg/mL, many rhodamine red fluorescent dye-included PLA nanoparticles were incorporated into the stem cells.

Next, in order to study how long the adipose-derived stem cells which have taken up the simvastatin-included PLA nanoparticles take to release statin from the cells, the amount of the statin released into the medium was measured. Here, similarly to the above test, after the adipose-derived stem cells were treated with simvastatin-included PLA nanoparticles at a concentration of 100 µg/mL for one hour, the medium was replaced, and the amount of simvastatin released in the medium was measured 6 hours, 18 hours, 24 hours, 48 hours, 72 hours, 120 hours, 168 hours, and 336 hours after the replacement of the medium. Specifically, the measurement was performed by using a High-pressure Liquid Chromatography (HPLC) method. The measurement results are shown in FIG. 2.

Figure 2:
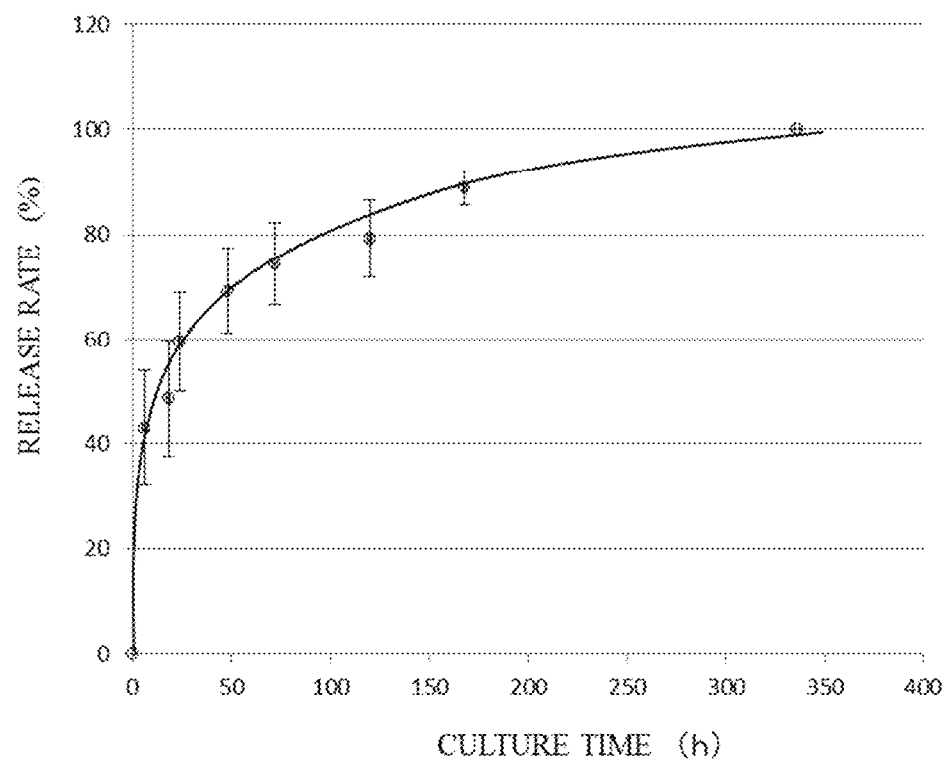
FIG. 2 is a graph illustrating the amount of simvastatin released from adipose-derived stems cell into a medium, the amount being measured after treatment of the adipose-derived stem cell with simvastatin-included PLA nanoparticles at a concentration of 100 μg/mL for one hour.

As shown in FIG. 2, about 60% of statin were released from the adipose-derived stem cells 24 hours from the start of the measurement, and it took about 336 hours to release all statin. From this result, it can be seen that the statin incorporated into the adipose-derived stem cells is not rapidly released but is gradually released from the adipose-derived stem cells. Thus, almost all statin is not released before the adipose-derived stem cells reach the ischemic myocardium, and after the adipose-derived stem cells reach the diseased part, statin can be released over a long time, so that a good therapeutic effect can be expected.

Next, in order to study enhancement of functions such as the migratory capacity, the proliferation capacity, and the productivity of the neovascularization factor of the adipose-derived stem cells due to the simvastatin-included nanoparticles, the following test was conducted.

First, the migratory capacity of the adipose-derived stem cells was studied by using a migratory property test kit (Transwell (registered trademark)). Specifically, adipose-derived stem cells were seeded on a porous membrane of each of wells of the Transwell plate at a dose of $5 \times 10^4$ cells/well, and in the media, statin-non-included PLA nanoparticles were added to achieve a concentration of 20 µg/mL, and simvastatin-included PLA nanoparticles were added to achieve a concentration of 20 µg/mL, 50 µg/mL, and 100 µg/mL. After 16 to 18 hours, the number of cells passed through the membrane of the Transwell was measured. The measurement results are shown in FIG. 3(a).

Figure 3:
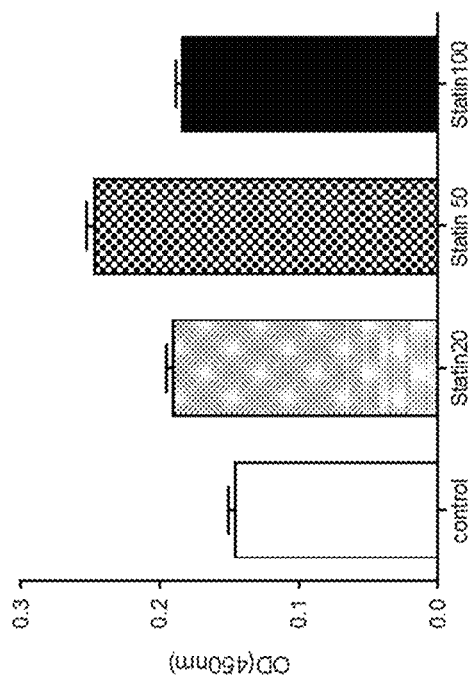
FIG. 3(a) is a graph illustrating measurement results of the migratory property of the adipose-derived stem cells treated with PLA nanoparticles or statin-included PLA nanoparticles.
FIG. 3(b) is a graph illustrating measurement results of the proliferation characteristic of the adipose-derived stem cells treated with statin-included PLA nanoparticles.
Figure 3:
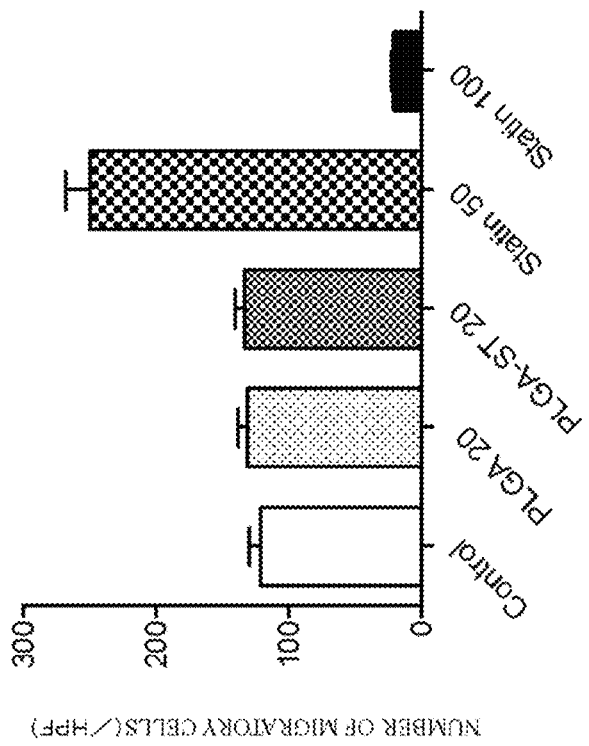

As shown in FIG. 3(a), in the case of treatment with 20-µg/mL statin-non-included PLA nanoparticles (PLA20), and in the case of treatment with 20-µg/mL simvastatin-included PLA nanoparticles (PLA-ST20), the migratory property of the adipose-derived stem cell did not change as compared to the case of a control group (Control) without the treatment, but in the case of treatment with 50-µg/mL simvastatin-included PLA nanoparticles (Statin50), the migratory property of the adipose-derived stem cells increased. Moreover, treatment with 100-µg/mL simvastatin-included PLA nanoparticles (Statin100) resulted in a reduction in the migratory property of the adipose-derived stem cells. These results show that the simvastatin-included PLA nanoparticles can promote the migratory capacity of the adipose-derived stem cells although there is an optimal treatment concentration.

Next, results of study of an improvement in the proliferation characteristic of the adipose-derived stem cells due to the simvastatin-included nanoparticles by an MTT assay will be described.

First, adipose-derived stem cells were seeded on a 96-well microplate at 5000 cells/well, simvastatin-included PLA nanoparticles were added to achieve a concentration of 20 µg/mL, 50 µg/mL, or 100 µg/mL, the medium was replaced after 48 hours, an MTT solution was added to each well, and after two hours, the optical density at 450 nm was measured with a spectral photometer. The measurement results are shown in FIG. 3(b).

As shown in FIG. 3(b), in all the cases of treatment with the simvastatin-included nanoparticles at concentrations of 20 µg/mL (Statin20), 50 µg/mL (Statin50), and 100 µg/mL (Statin100), the proliferation of the adipose-derived stem cells was observed as compared to the case of a control group (Control) without the treatment, but in particular, in the case of the treatment at a concentration of 50 µg/mL, a significant increase in the proliferation characteristic was observed as compared to the control group. These results show that the simvastatin-included PLA nanoparticles can promote the proliferation capacity of the adipose-derived stem cells.

Next, in order to study the effect of the simvastatin-included nanoparticles on the neovascularization factor productivity of the adipose-derived stem cell, the mRNA expression amount of the neovascularization factors in the adipose-derived stem cells was analyzed by a quantitative PCR method. Here, as the neovascularization factor, mRNA expression amounts of VEGF-A, VEGF-C, and FGF-2 in the cell were measured.

Figure 4:
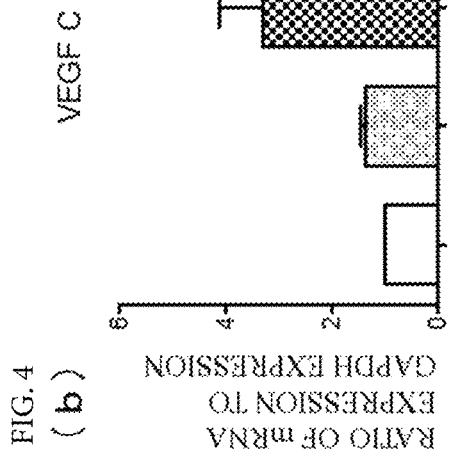
Figure 4:
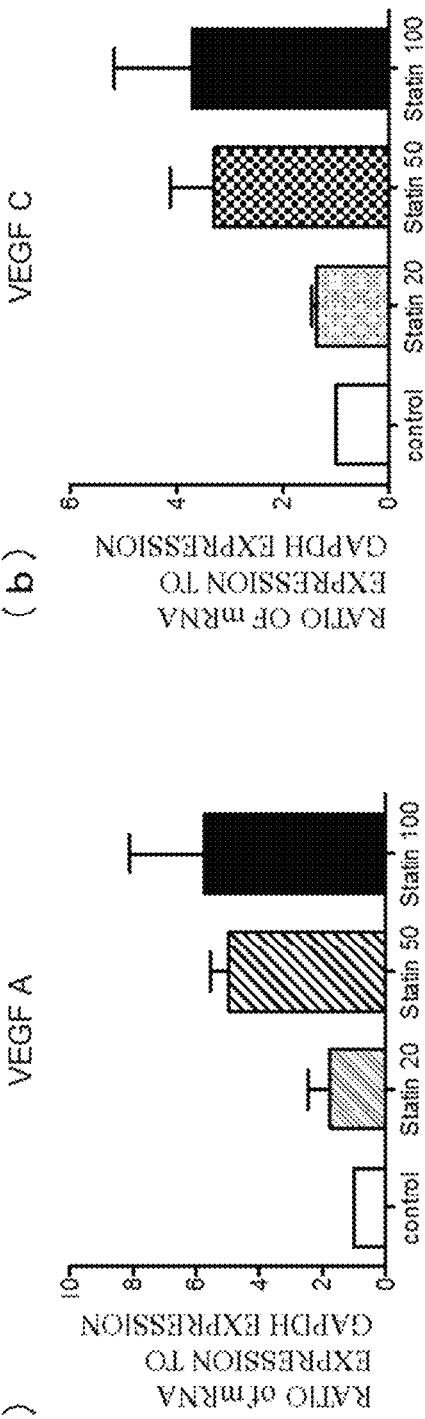
Figure 4:
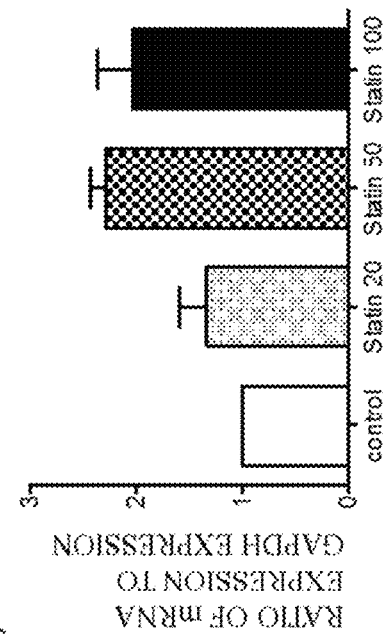

First, to incubate media for incubation of the adipose-derived stem cells, simvastatin-included PLA nanoparticles were added to achieve a concentration of 20 µg/mL, 50 µg/mL, and 100 µg/mL, and after 24 hours, the cells treated at each of the concentrations were collected, and RNA of each cell was extracted with a NucleoSpin RNA kit (Takara Bio Inc.). Then, the mRNA expression amounts of VEGF-A, VEGF-C, and FGF-2 in each cell was measured by using a primer relating to DNA sequences of VEGF-A, VEGF-C, and FGF-2 by the quantitative PCR method. The measurement was performed in such a manner that cDNA was synthetized from RNA extracted by using a ReverTra Ace qPCR RT kit (TOYOBO), a reaction together with SsoFast EvaGreen Mastermix reagent (Bio-Rad) and a primer (VEGF-A: F-TTACTCTCACCTGCTTCT (SEQ ID NO: 1), R-CTGCTTCTTCCAACAATG (SEQ ID NO: 2), VEGF-C: F-TCAAGGACAGAAGAGACTA (SEQ ID NO: 3), R-CCACATCTATACACACCTC (SEQ ID NO: 4), FGF-2: F-TTCTTCCAATGTCTGCTAA (SEQ ID NO: 5), R-GAC-CAATTATCCAAACTGAG (SEQ ID NO: 6)) was performed by using Thermal Cycler (CFX Connect Bio-Rad) according to the manufacturer's instructions (one cycle of 95° C. and 30 seconds, and 40 cycles of 95° C. and 5 seconds/56° C. and 5 seconds). The measurement results are shown in FIG. 4(a)-FIG. 4(c). Note that the results show the ratio of the expression amount of each of the factors with reference to the mRNA expression amount of GAPDH.

As shown in FIG. 4(a), in the case of treatment with the simvastatin-included nanoparticles at a concentration of 20 μg/mL (Statin20), 50 μg/mL (Statin50), and 100 μg/mL (Statin100), the mRNA expression amount of VEGF-A increased as compared to the case of a control group (Control) without the treatment, and in particular, in the case of treatment with the simvastatin-included nanoparticles at a concentration of 100 μg/mL, a significant increase was observed.

As shown in FIG. 4(b), in the case of treatment with the simvastatin-included nanoparticles at a concentration of 20 μg/mL (Statin20), 50 μg/mL (Statin50), and 100 μg/mL (Statin100), the mRNA expression amount of VEGF-C increased as compared to the case of a control group (Control) without the treatment, and in particular, in the case of treatment with the simvastatin-included nanoparticles at a concentration of 50 μg/mL or 100 μg/mL, a significant increase was observed.

Similarly, as shown in FIG. 4(c), in the case of treatment with the simvastatin-included nanoparticles at a concentration of 20 μg/mL (Statin20), 50 μg/mL (Statin50), and 100 μg/mL (Statin100), the mRNA expression amount of FGF-2 increased as compared to the case of a control group (Control) without the treatment, and in particular, in the case of treatment with the simvastatin-included nanoparticles at a concentration of 50 μg/mL or 100 μg/mL, a significant increase was observed. These results show that the simvastatin-included PLA nanoparticles can promote the neovascularization factor productivity of the adipose-derived stem cells.

As described above, the enhancement of functions such as the migratory capacity, the proliferation capacity, and the productivity of the neovascularization factor of the adipose-derived stem cells due to the simvastatin-included nanoparticles was studied. As a conclusion, the statin-included nanoparticles can enhance the functions of the adipose-derived stem cells. These functions are functions of accumulating the adipose-derived stem cells at an ischemic myocardium part after administration of the adipose-derived stem cells in a living body so as to advantageously function to regenerate the ischemic myocardium part. When these functions are enhanced, the adipose-derived stem cells are very advantageous for the treatment of ischemic heart diseases such as a myocardial infarction.

Next, with a myocardial infarction model mouse, therapeutic effect of statin-included nanoparticles according to the present invention and stem cells containing the statin-included nanoparticles on the myocardial infarction was studied.

Figure 6:
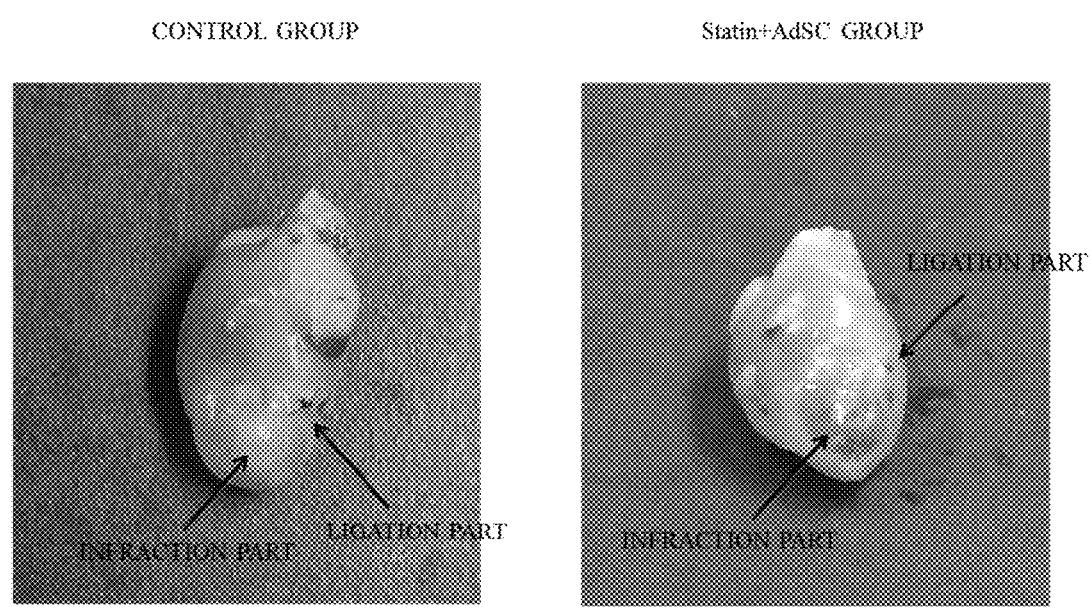
FIG. 6 shows photographs of the hearts of the myocardial infarction model mice 28 days after administration of the adipose-derived stem cells which have taken up the statin-included nanoparticles or administration of PBS.

First, in each of 12-week-old male BALB/c nude mice, an ischemia was induced (anterior descending coronary artery ligation model), and a heart ultrasonic image diagnosis was performed on each 12-week-old male BALB/c nude mouse (day 0). After three days (day 3) from the diagnosis, phosphate buffer saline (PBS), the adipose-derived stem cells which had been obtained as described above and had taken up statin-non-included PLA nanoparticles, the adipose-derived stem cells which had been obtained as described above and had taken up the statin-included PLA nanoparticles, or statin-included PLA nanoparticles were administered to the mice via their caudal veins. Note that as the adipose-derived stem cells which had taken up the statin-capsulated PLA nanoparticles, adipose-derived stem cells treated with statin-included nanoparticles at a concentration of 100 μg/mL for one hour were used. The dose of the adipose-derived stem cells was $1 \times 10^4$ cells/mouse, and the dose of the statin-included PLA nanoparticles was 50 μg/mouse. Moreover, on the day (day 3), the heart ultrasonic image diagnosis was also conducted. After 11 days after the heart ultrasonic image diagnosis (on the day 14), the heart ultrasonic image diagnosis was conducted again. Then, 14 days later (on day 28), the heart ultrasonic image diagnosis was conducted again, and then an autopsy was performed to perform a histologic analysis. In the heart ultrasonic image diagnosis, the left ventricular ejection fraction (EF), the left ventricular fractional shortening (FS), the left ventricular end-diastolic dimension (LVDd), and the left ventricular end-systolic dimension (LVDs) were measured. In the histologic analysis, the capillary vessel density, the ratio of fiberized areas, the adipose-derived stem cell taking rate, and the adipose-derived stem cell differentiation frequency were analyzed. FIG. 5(a)-FIG. 5(d) show results of the heart ultrasonic image diagnosis. FIG. 6 shows hearts taken out of the mice on day 28. FIG. 7(a), FIG. 7(b), FIG. 7(c), FIG. 8, and FIG. 10 to FIG. 17 show results of the histologic analysis. Moreover, FIG. 9(a)-FIG. 9(e) show the heart and parts around the heart taken out of the mouse 60 days after the administration of the adipose-derived stem cells which had taken up the statin-capsulated PLA nanoparticles.

As shown in FIG. 5(a) and FIG. 5(b), in all groups, the EF and the FS decreased, and the function of the heart degraded on day 3, and then, on day 14 and day 28, no improvement was observed in the control group (PBS: ●) without treatment, whereas a slight improvement was observed in a group (PLA+AdSC: ▲) administered with the adipose-derived stem cells which had taken up the statin-non-included PLA nanoparticles and a group (Statin/PLA: ▼) administered with the statin-capsulated PLA nanoparticles. Moreover, a significant improvement was observed in a group (Statin/PLA+AdSC:■) administered with the at-derived stem cells which had taken up the statin-capsulated PLA nanoparticles. Moreover, as shown in FIG. 5(c) and FIG. 5(d), also an increase in the LVDd and the LVDs was restricted in the group (Statin/PLA+AdSC:■) administered with the adipose-derived stem cells which had taken up the statin-included nanoparticles as compared to the control group (PBS:●) without treatment, the group (PLA+AdSC: ▲) administered with the adipose-derived stem cells which had taken up the statin-non-included PLA nanoparticles, and the group (Statin/PLA: ▼) administered with the statin-capsulated PLA nanoparticles, and an improvement in the cardiac function was observed.

Moreover, as shown in FIG. 6, it can be apparently observed that the expansion of the heart (photograph on the right) of the group administered with the adipose-derived stem cells which had taken up the statin-included nanoparticles is restricted as compared to the control group (photograph on the left).

Moreover, FIG. 7(a) to FIG. 7(c) show results of evaluation of the cardiac muscle wall cross-section area of a cut piece of an infract part of a heart taken out of each of the groups, the cut piece being Mason-trichrome stained. FIG. 7(a) shows photographs of stained cut pieces, wherein fiberized scar parts are stained blue and are indicated by arrows. FIG. 7(b) shows the length of each fiberized part which is stained blue (length indicated by the arrow in FIG. 7(a)) as a proportion to the length of the entire periphery of the fiberized part, where the length of the entire periphery is defined as 100%. FIG. 7(c) shows the thicknesses of each of cardiac muscle walls of the fiberized parts which are stained blue as a proportion to the thickness of a normal cardiac muscle wall, where the thickness of the normal cardiac muscle wall is defined as 100%.

As shown in FIG. 7(a) and FIG. 7(b), the length of the fiberized scar part stained blue in the group (AdSC+Statin/PLA) administered with the adipose-derived stem cells which had taken the statin-included nanoparticles is shorter than that in the control group (Control) without treatment, the group (PLA+AdSC) administered with the adipose-derived stem cells which had taken up the statin-non-included PLA nanoparticles, and the group (Statin/PLA) administered with statin-capsulated PLA nanoparticles. Moreover, as shown in FIG. 7(a) and FIG. 7(c), the thickness of the cardiac muscle wall became large in the group administered with the adipose-derived stem cells which had taken up the statin-included nanoparticles as compared to the other groups, which suggests that the regeneration of the cardiac muscle part is promoted.

Figure 8:
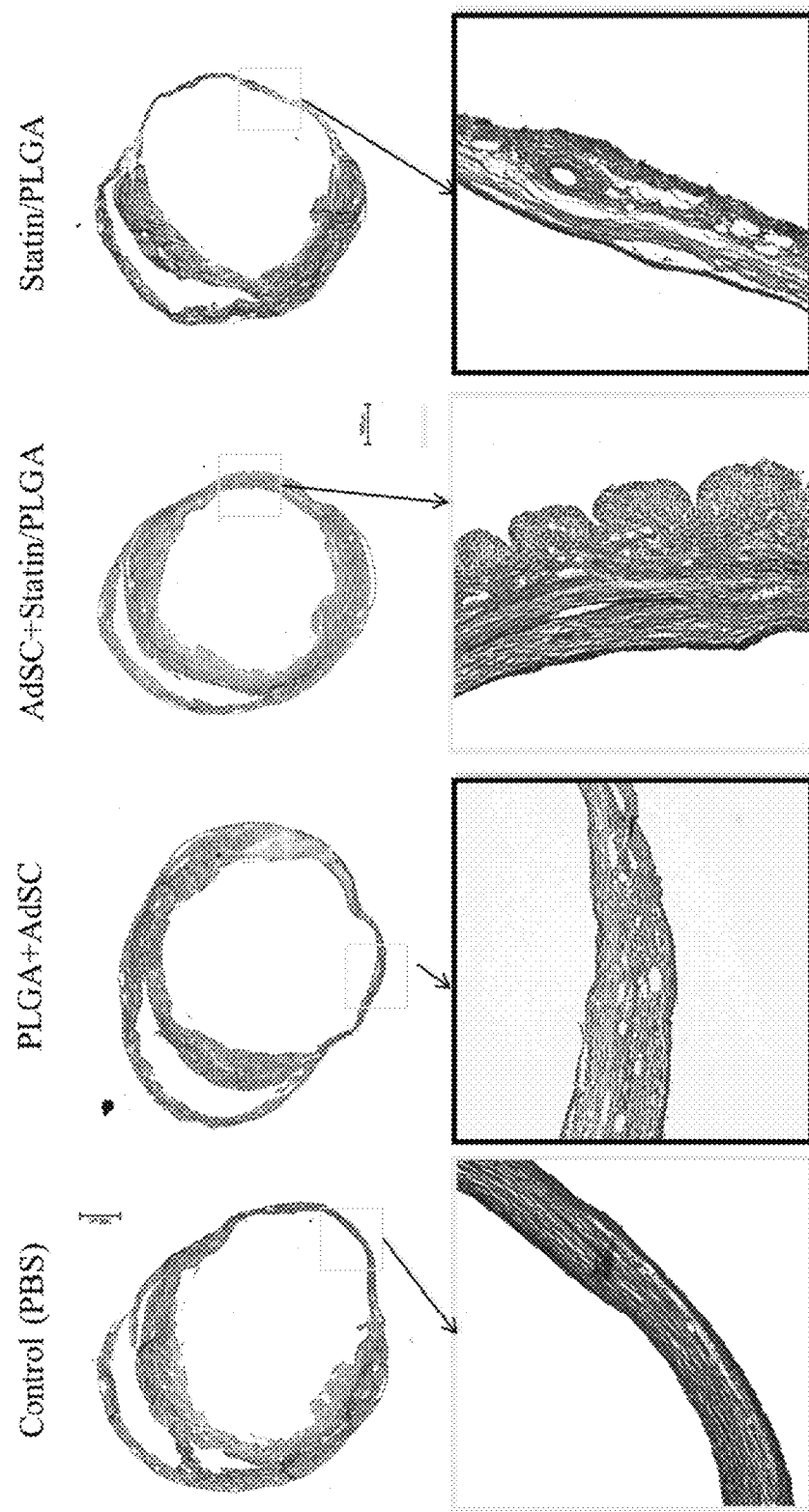
FIG. 8 shows photographs of Masson-trichrome stained cut pieces of infract parts of the heart of the myocardial infarction model mice administered with PBS, statin-included nanoparticles, adipose-derived stem cells which have taken up statin-non-included nanoparticles, or adipose-derived stem cells which have taken up statin-included nanoparticles, wherein fiberized parts are enlarged.

FIG. 8 shows photographs showing enlarged views of fiberized parts of the cut pieces of the groups. As shown in FIG. 8, in the control group (Control), the cut piece shows flat appearance and almost all parts are stained blue, whereas in the group (PLA+AdSC) administered with the adipose-derived stem cells which had taken up the statin-non-included PLA nanoparticles and the group (Statin/PLA) administered with statin-capsulated PLA nanoparticles, some parts were slightly stained red but no significant difference from the control group were observed. On the other hand, in the group (AdSC+Statin/PLA) administered with the adipose-derived stem cells which had taken up the statin-included nanoparticles, parts bulging out of the fiberized cardiac muscle being stained red were observed. These parts were not observed in the other groups and it can be supposed that these parts are parts in the course of regeneration of new cardiac muscle due to the adipose-derived stem cells which have taken up the statin-included nanoparticles.

Figure 7:
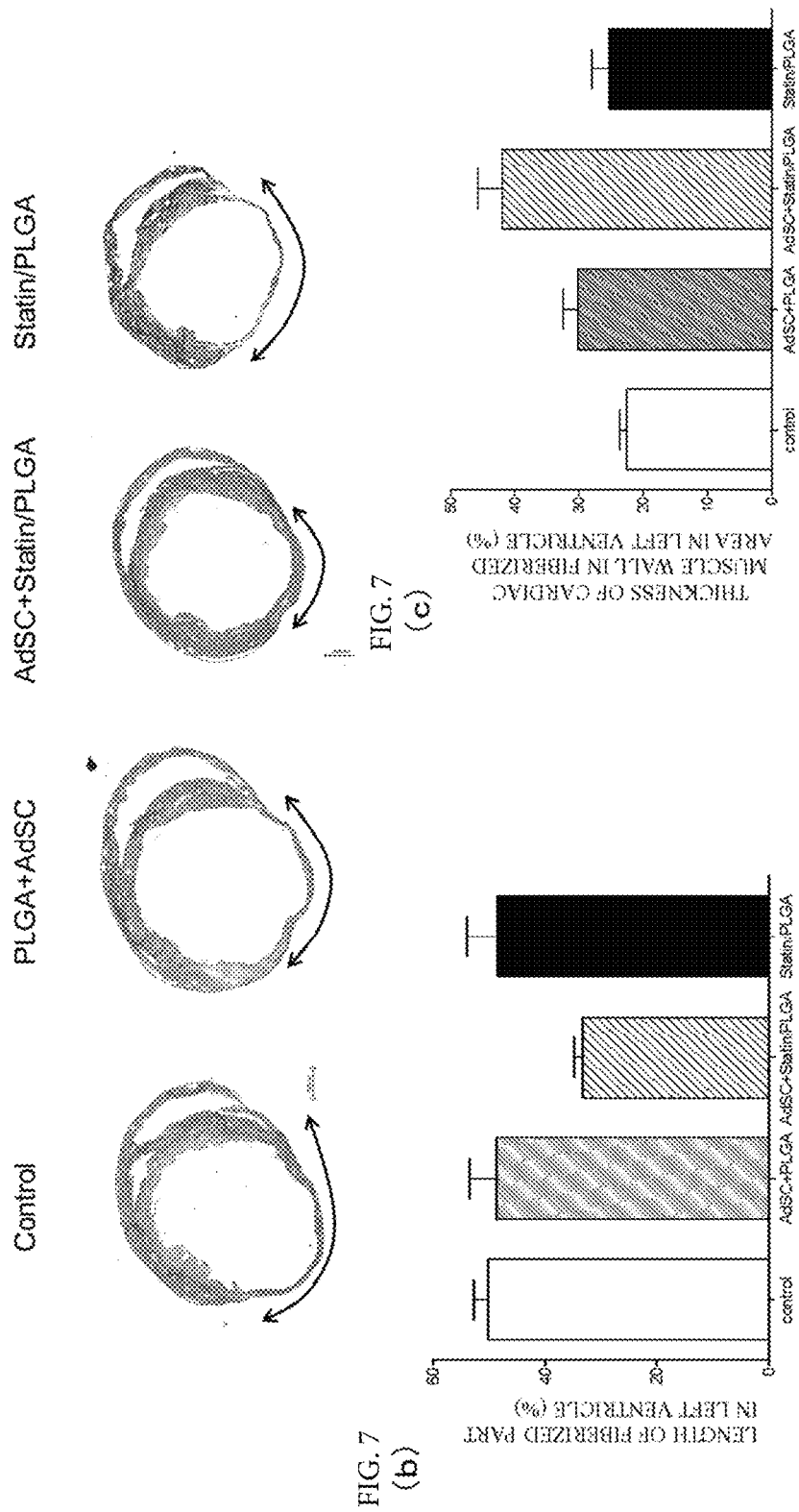
FIG. 7(a) shows photographs of Masson-trichrome stained cut pieces of infract parts of the heart of the myocardial infarction model mice administered with PBS, statin-included nanoparticles, adipose-derived stem cells which have taken up statin-non-included nanoparticles, or adipose-derived stem cells which have taken up statin-included nanoparticles.
FIG. 7(b) is a graph illustrating the length of fiberized part of each of the cut pieces.
FIG. 7(c) is a graph illustrating the thickness of the cardiac muscle wall of the fiberized part of each of the cut pieces.
Figure 9:
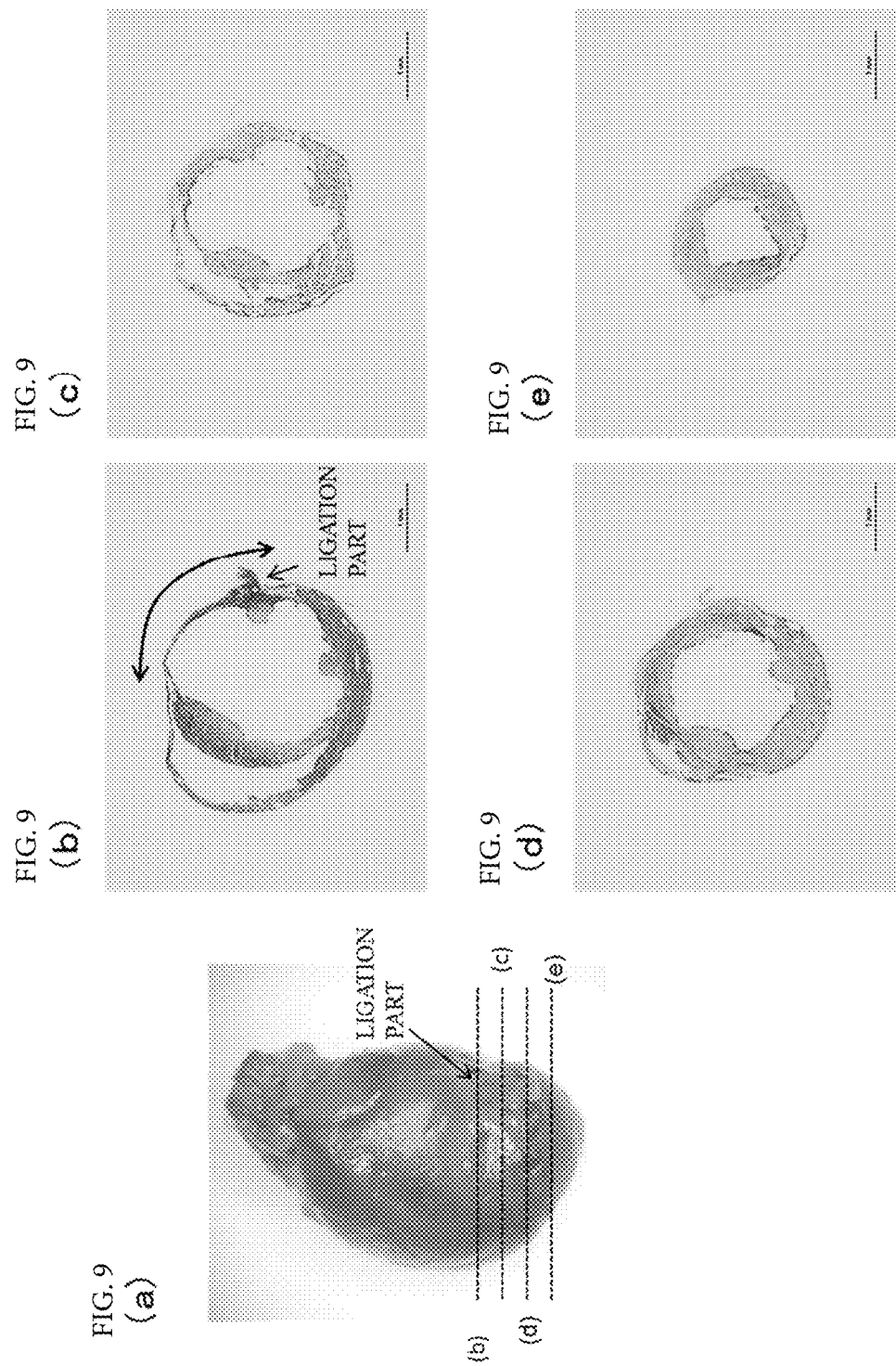
FIG. 9(a) is a photograph of the heart of the myocardial infarction model mouse 60 days after administration of the adipose-derived stem cells which have taken up statin-included nanoparticles.
FIG. 9(b) to FIG. 9(e) are photographs of Masson-trichrome stained cut pieces respectively taken along lines (b) to (e) of FIG. 9(a).

Moreover, in FIG. 6 to FIG. 8, the hearts of the mice 28 days after the administration of the adipose-derived stem cells which had taken the statin-included nanoparticles were shown, but in order to confirm the therapeutic effect thereafter, appearances of the hearts of the mice 60 days after the administration of the adipose-derived stem cells which had taken the statin-included nanoparticles were observed, and cut pieces of different parts of the hearts were stained and observed in the same manner as described above. The results are shown in FIG. 9(a) to FIG. 9(e). Note that FIG. 9(a) is a photograph of a heart of the mouse, and FIG. 9(b) to FIG. 9(e) are photographs of Masson-trichrome stained pieces respectively taken along lines (b) to (e) of FIG. 9(a). Note that the curved arrow in FIG. 9(b) indicates an area stained blue.

As shown in FIG. 9(a), 60 days after the administration of the adipose-derived stem cells which had taken up the statin-included nanoparticles, an infract (fiberized) part observed 28 days after the administration tended to be scaled down. Moreover, as shown in FIG. 9(b) to FIG. 9(e), each of the cut pieces of the infract part has a large thickness of the cardiac muscle wall, and most parts except for the ligation part shown in FIG. 9(b) were stained red, and therefore, regeneration of the cardiac muscle part is considered to be promoted. From these results, 60 days after the administration of the adipose-derived stem cells which had taken up the statin-included nanoparticles, a therapeutic effect of regeneration of the functional cardiac muscle is observed.

Figure 10:
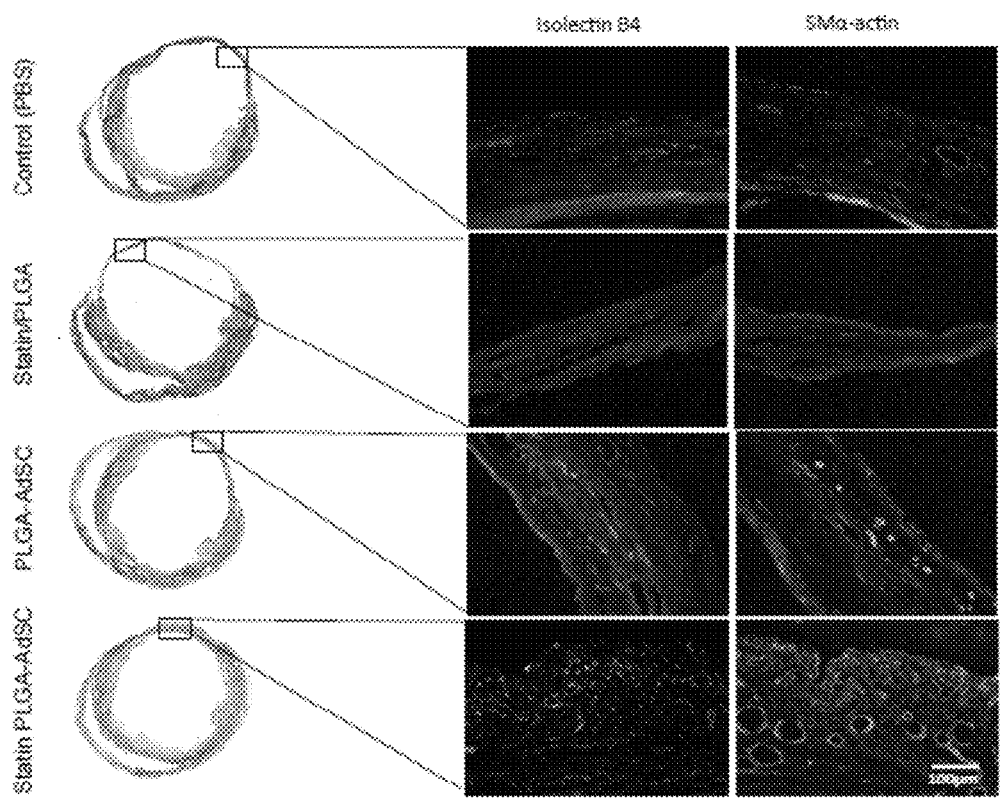
FIG. 10 shows photographs of cut pieces of infract parts of the heart of the myocardial infarction model mice administered with PBS, statin-included nanoparticles, adipose-derived stem cells which have taken up statin-non-included nanoparticles, or adipose-derived stem cells which have taken up statin-included nanoparticles, wherein the respective cut pieces immunostained with isolectin B4 and an anti-SMα actin antibody are shown.

Next, in order to study the neovascularization in the cardiac muscle tissue in the infract part, the cut pieces were immunostained by using respective antibodies or the like bonded to glycoprotein expressed in a vascular endothelial cell and protein expressed in a vascular smooth muscle cell, and the results are shown in FIG. 10. Specifically, as the respective antibodies or the like, isolectin B4 of a fluorescein isothiocyanate (FITC) marker which is plant-derived protein that binds to glycoprotein expressed in the vascular endothelial cell and a rabbit-derived IgG antibody that binds to SMa actin which is a protein expressed in the vascular smooth muscle cell were used, and as the secondary antibody for the rabbit-derived IgG, an Alexa 488-goat-derived anti-rabbit IgG antibody was used for staining the cut pieces.

As shown in FIG. 10, in the control group (Control (PBS)), the cut pieces were hardly stained in both the case where the FITC-isolectin B4 (Isolectin B4) was used and the case where the anti-SMα-actin antibody (SMα-actin) was used, that is, almost no vascular endothelial cell and almost no vascular smooth muscle cell were detected, and almost no blood vessel may exist. Moreover, also in the group (Statin/PLGA) administered with the statin-included nanoparticles, almost no vascular endothelial cell and almost no vascular smooth muscle cell were detected, and in the group (PLA-AdSC) administered with the adipose-derived stem cells which had taken up the statin-non-included nanoparticles, few vascular endothelial cells and few vascular smooth muscle cells were detected. In contrast, in the group (Statin PLA-AdSC) administered with the adipose-derived stem cells which had taken up the statin-included nanoparticles, many areas were stained, and it can be supposed that the neovascularization occurred. That is, the administration of the adipose-derived stem cells having taken up statin-included nanoparticles is considered to promote regeneration of vascular tissues in the cardiac muscle.

Next, the vascular density in an ischemia borderline region was studied. Specifically, a fiberized part of each group was subjected to fluorescent staining with FITC-isolectin B4 in a manner similar to the above-described analysis, and the size of a stained area in a microscopic field was measured. Measurement results were put into a graph of vascular densities. The results are shown in FIG. 11(a) and FIG. 11(b).

As shown in FIG. 11(a) and FIG. 11(b), the vascular density slightly increased in the group (PLA+AdSC) administered with the adipose-derived stem cells which had taken up the statin-non-included PLA nanoparticles and in the group (Statin/PLA) administered with statin-capsulated PLA nanoparticles as compared to the control group (Control (PBS)). Moreover, as compared to these groups, an increase in the vascular density was confirmed in the group (Statin/PLA+AdSC) administered with the adipose-derived stem cells which had taken up the statin-included nanoparticles. Also from these results, it can be considered that administration of the adipose-derived stem cells having taken up the statin-included nanoparticles promotes neovascularization at a part (ischemic part) in the periphery of the infract and contributes to cardiac muscle tissue regeneration.

Figure 12:
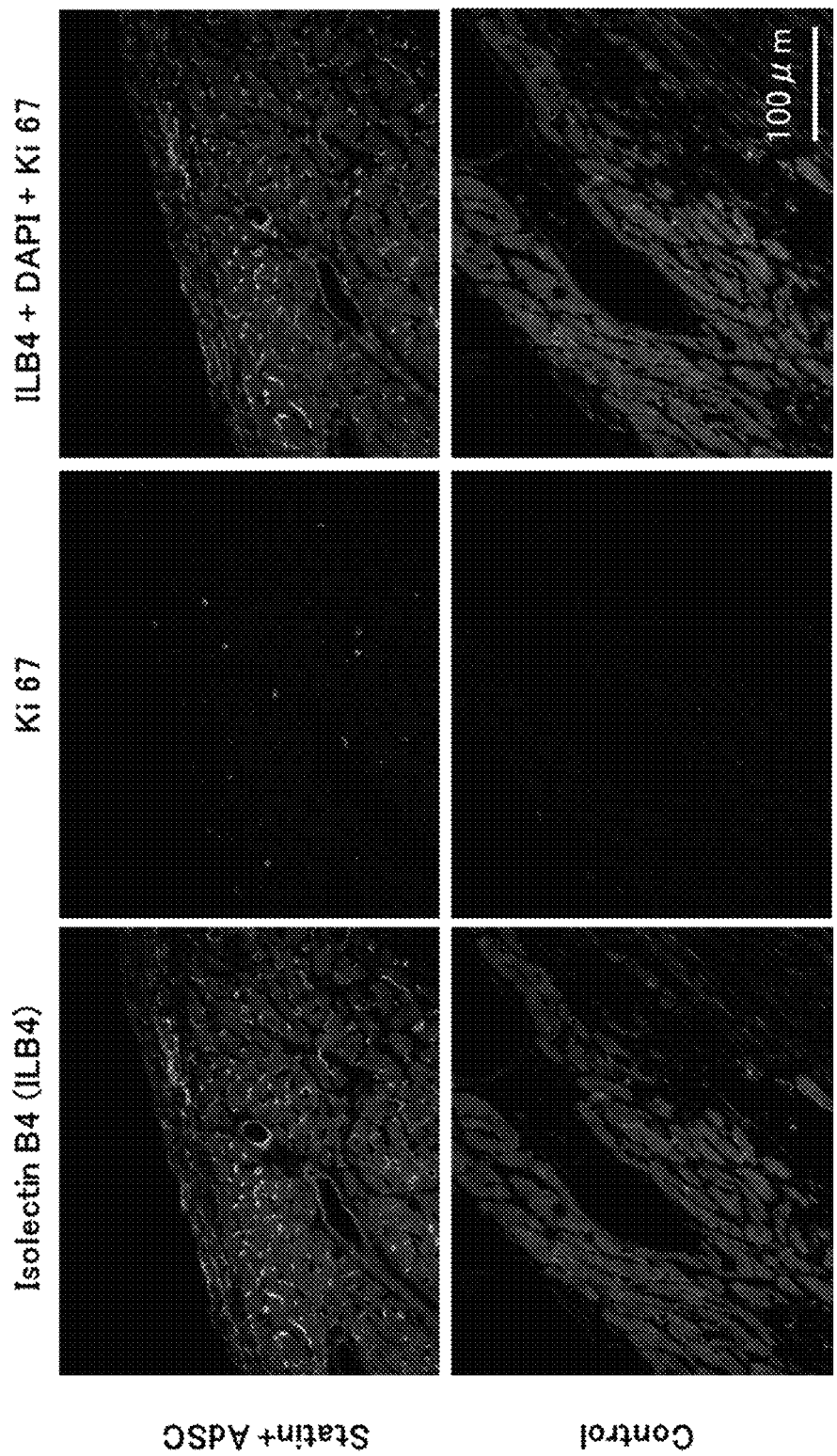
FIG. 12 shows photographs of cut pieces of an infract part of the heart of a myocardial infarction model mouse administered with adipose-derived stem cells which have taken up statin-included nanoparticles, the cut pieces being immunostained with isolectin B4 and an anti-Ki67 antibody.

Next, in order to study the cell proliferation activity in the ischemic myocardium tissue, the cut pieces were immunostained by using an antibody that binds to Ki67 protein expressed in the proliferation phase of a cell, and results are shown in FIG. 12. Specifically, a vascular endothelial cell and a cell in the proliferation phase of fiberized parts of the control group and the group administered with the adipose-derived stem cells which had taken up the statin-included nanoparticles were immunostained with FITC-isolectin B4, a rabbit-derived anti-Ki67 antibody, and an Alexa 594-goat-derived anti-rabbit IgG antibody as a secondary antibody.

As illustrated in FIG. 12, in control group (Control) without treatment, staining was not observed in either of the cases of the antibodies. However, in the group (Statin+AdSC) group administered with the adipose-derived stem cells which had taken up the statin-included nanoparticles, not only staining with the FITC-isolectin B4 in a manner similar to the above test, but also staining with the anti-Ki67 antibody was observed. This result suggests that administration of the adipose-derived stem cells having taken up the statin-included nanoparticles promotes the cell proliferation activity in the ischemic myocardium tissue. Moreover, parts stained with the isolectin B4 are different from parts stained with the Ki67, and therefore, it is considered that cells which proliferate are cells (e.g., stromal fibroblasts) that are different from vascular endothelial cells forming capillary vessels.

Figure 13:
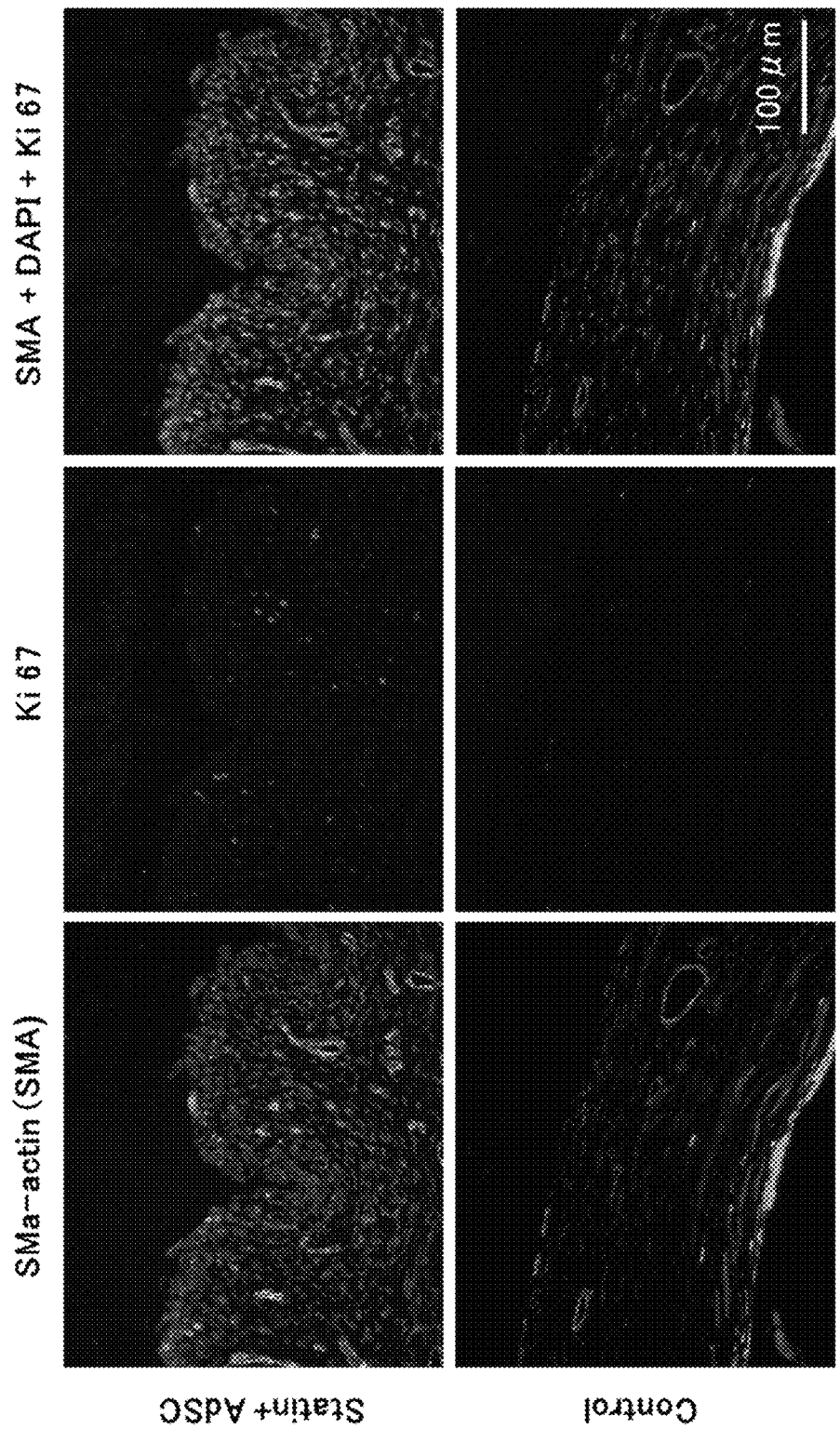
FIG. 13 shows photographs of cut pieces of an infract part of the heart of a myocardial infarction model mouse administered with adipose-derived stem cells which have taken up statin-included nanoparticles, the cut pieces being immunostained with an anti-SMα-actin antibody and an anti-Ki67 antibody.

Moreover, FIG. 13 shows cut pieces immunostained with the anti-SMα-actin antibody and an anti-Ki67 antibody in a manner similar to the above described manner. As shown in FIG. 13, also in this case, the cut pieces of the control group (Control) were hardly stained with either of the antibodies. In contrast, in the group (Statin+AdSC) administered with the adipose-derived stem cells which had taken up the statin-included nanoparticles, not only staining with the anti-SMα-actin antibody in a manner similar to the above test, but also staining with the anti-Ki67 antibody was observed. Moreover, parts stained with the anti-SMα-actin antibody are different from parts stained with the anti-Ki67 antibody, and therefore, it is considered that cells which proliferate are cells (e.g., stromal fibroblasts) that are different from smooth muscle cells.

Figure 14:
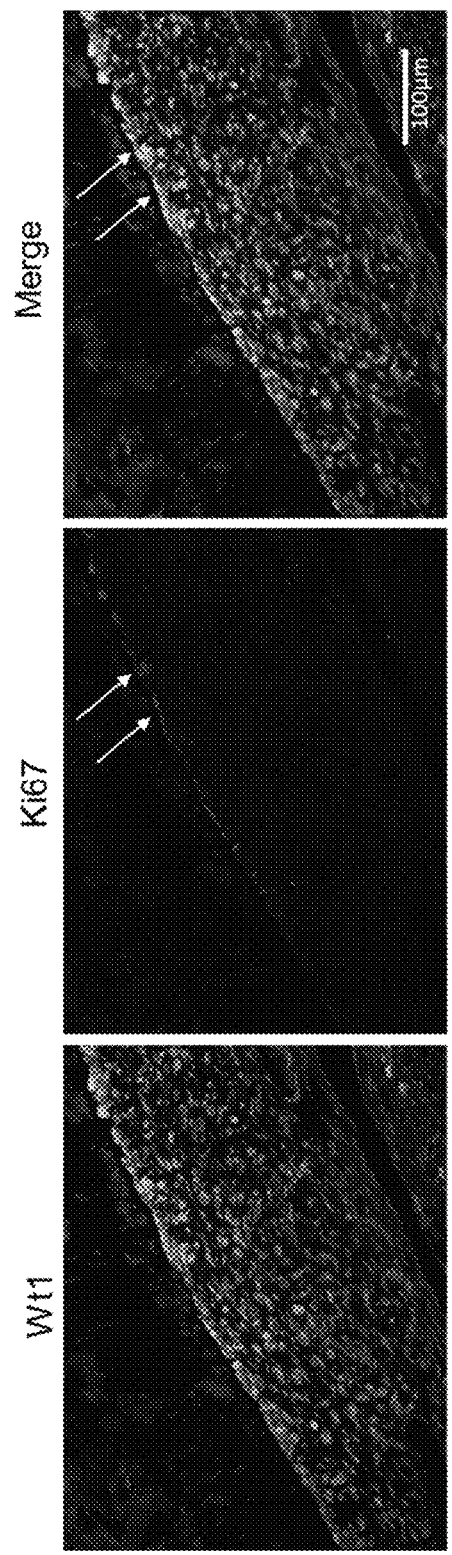
FIG. 14 shows photographs of cut pieces of an infract part of the heart of the myocardial infarction model mouse 14 days after administration of the adipose-derived stem cells which have taken up the statin-included nanoparticles, the cut pieces being immunostained with an anti-Wt1 antibody and the anti-Ki67.

Moreover, FIG. 14 shows cut parts of an infract part of the heart of the myocardial infarction model mouse 14 days after the administration of the adipose-derived stem cells which had taken up the statin-included nanoparticles, wherein the cut parts are immunostained with an anti-Wt1 antibody for staining Wt1 protein contained in the epicardium cell and the anti-Ki67 antibody in a manner similar to the above described manner. As shown in FIG. 14, many epicardium cells stained with the anti-Wt1 antibody were observed in the myocardial infarction part, and in the outermost part of the myocardial infarction part, many proliferation-phase cells which are stained with the anti-Ki67 antibody and with the anti-Wt1 antibody were observed (parts indicated by the arrow). This result suggests that in the infract part, epicardium cells are divided to proliferate outward while newly causing granulation, and thereby, the epicardium cells regenerate to increase the thickness of the cardiac muscle wall again. Thus, it can be assumed that, for example, even when one or more months have passed since the occurrence of myocardial infarction and most of infract parts have been in a scar state, administration of the adipose-derived stem cells having taken up the statin-included nanoparticles according to the claimed invention causes proliferation of epicardium cells remaining at the scar parts to promote regeneration of the cardiac muscle, and the myocardial infarction can be treated.

Figure 15:
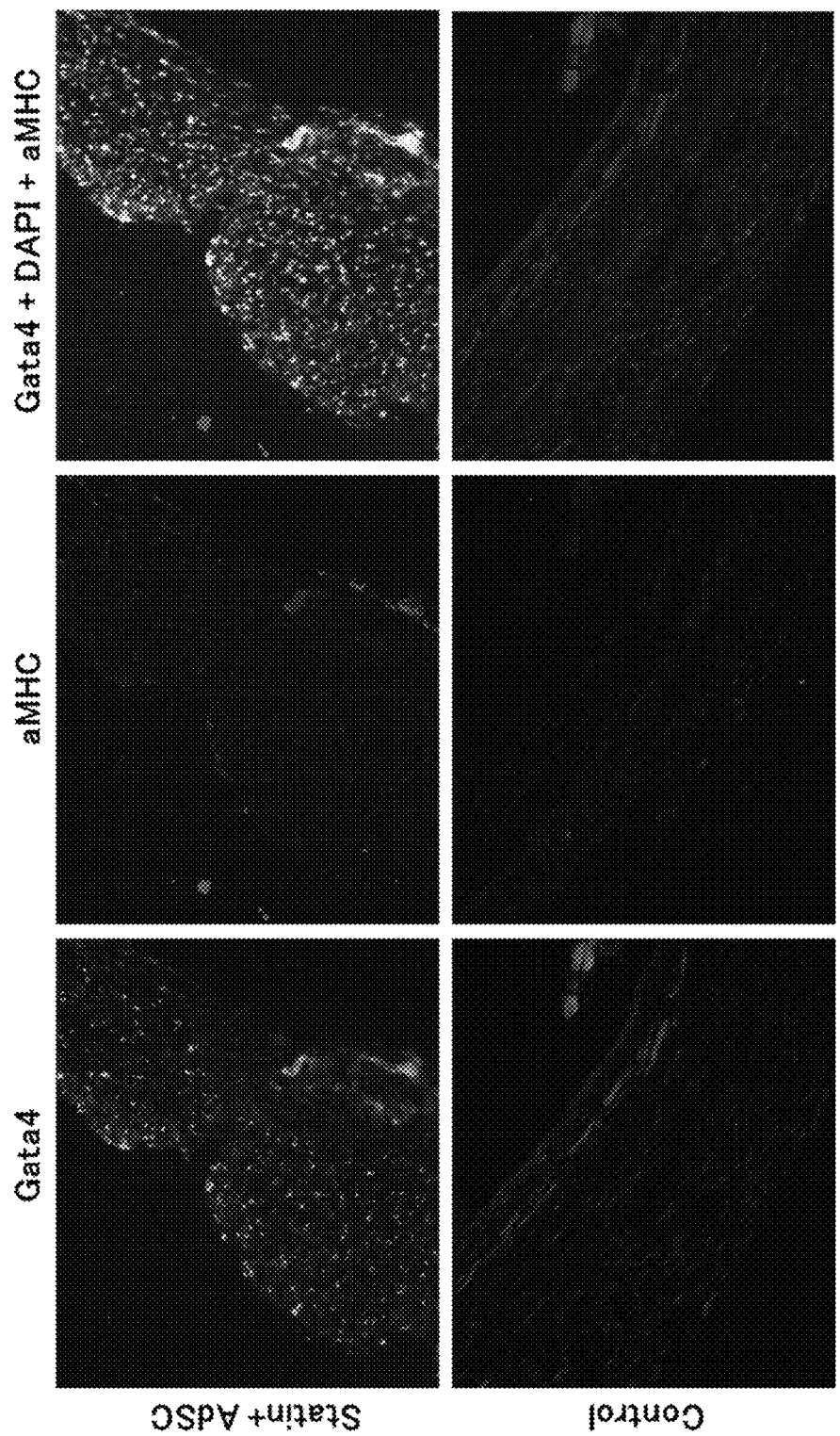
FIG. 15 shows photographs of cut pieces of an infract part of the heart of a myocardial infarction model mouse administered with adipose-derived stem cells which have taken up statin-included nanoparticles, the cut pieces being immunostained with an anti-GATA4 antibody and an anti-αMHC antibody are shown.

Next, in order to study regeneration of the cardiac muscle due to the adipose-derived stem cells which had taken up the statin-included nanoparticles, immunostaining was performed with an antibody that binds to protein expressed in the myocardial cell, and results are shown in FIG. 15. Here, as an antibody that binds to protein expressed in a myocardial cell, the rabbit-derived IgG antibody that binds to GATA4 also expressed in young myocardial cell, an Alexa 488 goat-derived anti-rabbit IgG antibody as a secondary antibody, a mouse-derived IgG antibody that binds to αMHC which is not expressed in a young myocardial cell but is expressed in only a myocardial cell, and an Alexa 594 goat-derived anti-mouse IgG antibody as secondary antibody were used.

As shown in FIG. 15, as a result of immunostaining with the GATA4, staining was hardly achieved in the control group (Control) without treatment, but in the group (Statin+AdSC) administered with the adipose-derived stem cells which had taken up the statin-included nanoparticles, many stained areas were detected. In contrast, the αMHC was immunostained, and staining was hardly observed in the control group, and in the group administered with the adipose-derived stem cells which had taken up the statin-included nanoparticles, few stained areas were observed, but the stained areas are significantly fewer than areas stained with the anti-GATA4 antibody.

Figure 16:
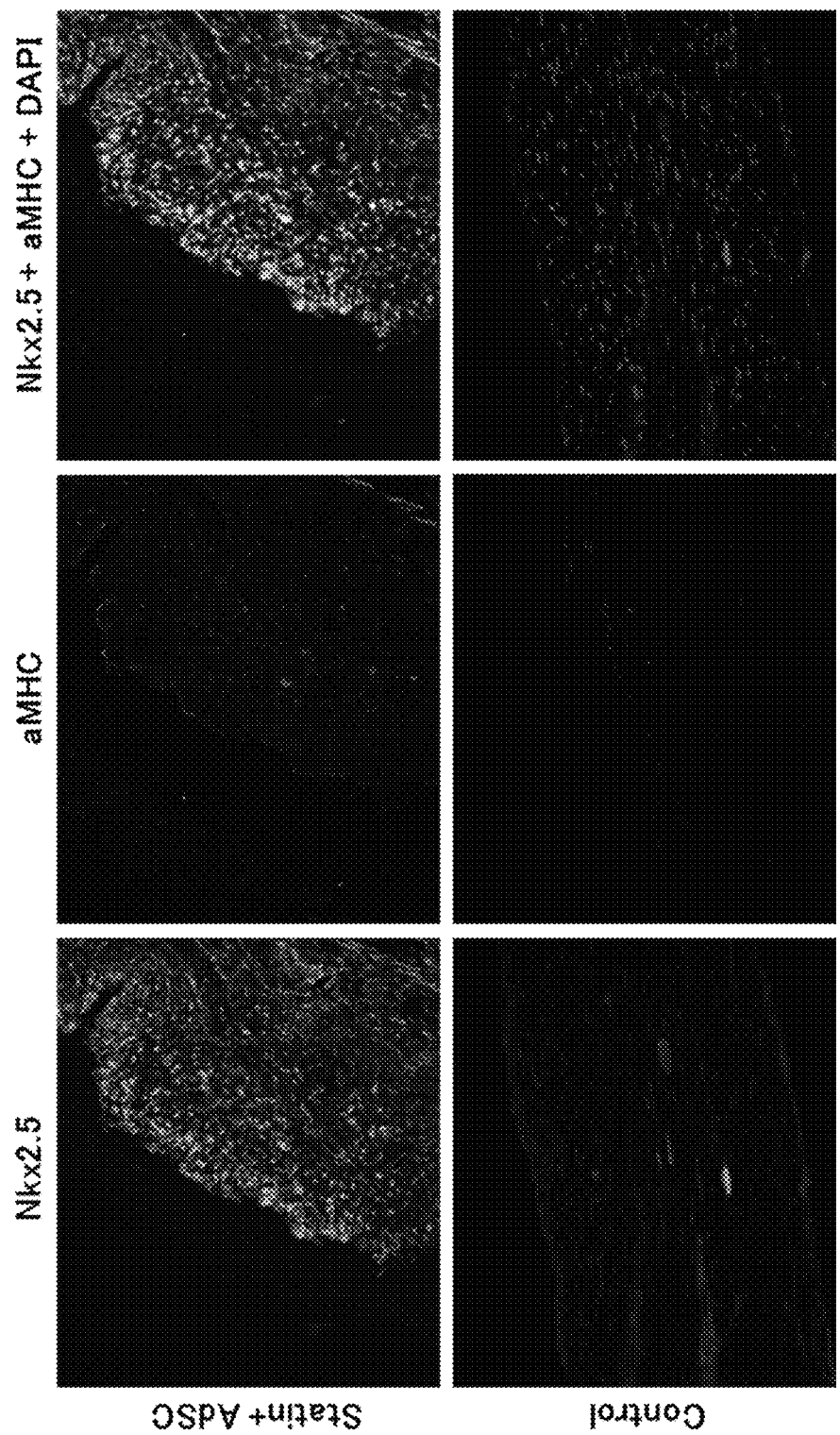
FIG. 16 shows photographs of cut pieces of an infract part of the heart of a myocardial infarction model mouse administered with adipose-derived stem cells which have taken up statin-included nanoparticles, the cut pieces being immunostained with an anti-Nkx2.5 antibody and an anti-αMHC antibody.

FIG. 16 shows results of immunostaining with the rabbit-derived IgG antibody of Nkx2.5 expressed in an immature myocardial cell in a manner similar to GATA4, an Alexa 488 goat-derived anti-rabbit IgG antibody as a secondary antibody, and the antibody of the αMHC in a manner similar to the immunostaining described above. As shown in FIG. 16, similar to the result of FIG. 15, as a result of immunostaining with the Nkx2.5 expressed in a young myocardial cell, staining was hardly achieved in the control group (Control) without treatment, but in the group (Statin+AdSC) administered with the adipose-derived stem cells which had taken up the statin-included nanoparticles, many stained areas were detected.

The results shown in FIG. 15 and FIG. 16 reveal that administration of the adipose-derived stem cells having taken up the statin-included nanoparticles cause expression of an immature myocardial cells in an ischemic myocardium tissue. That is, it is suggested that the adipose-derived stem cells having taken up the statin-included nanoparticles promotes regeneration of a cardiac muscle tissue.

In the experiments described above, results of the case where the adipose-derived stem cells having taken up the statin-included nanoparticles were administered to a myocardial infarction model mouse at $1 \times 10^4$ cells/mouse have been described. Next, regeneration of the cardiac muscle tissue in the case of administration at an amount of $5 \times 10^4$ cells/mouse was studied. For this purpose, myocardial infarction model mice prepared in the same manner as described above were administered with adipose-derived stem cells having taken up the statin-included nanoparticles via their caudal veins at $5 \times 10^4$ cells/mouse three days after ischemic treatment. The mice were subjected to autopsy 25 days after the administration and cut pieces of a myocardial infarction part were prepared. The cut pieces were immunostained with a rabbit-derived IgG antibody that binds to cardiac-muscle-type troponin (cTn-1) expressed in a cardiac muscle skeletal muscle cell, an Alexa 488 goat-derived anti-rabbit IgG antibody or the same anti-SMa actin antibody expressed in the smooth muscle cell as a secondary antibody, a rabbit-derived IgG antibody which binds to human mitochondria (hMtCd), and an Alexa 594 goat-derived anti-rabbit IgG antibody as a secondary antibody. The results are illustrated in FIG. 17.

Figure 17:
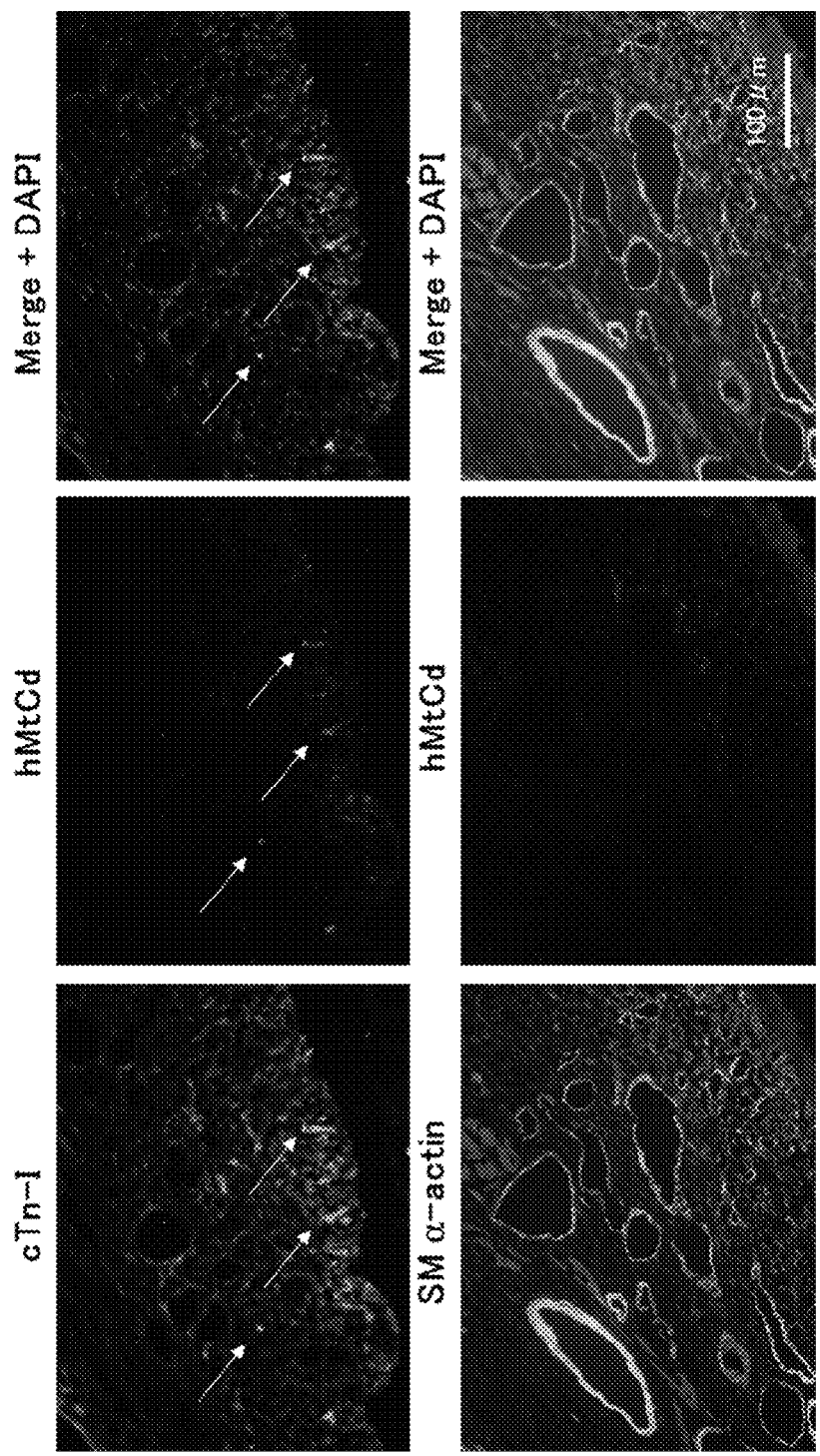
FIG. 17 shows photographs of cut pieces of an infarct part of the heart of a myocardial infarction model mouse administered with adipose-derived stem cells which have taken up statin-included nanoparticles, the cut pieces being immunostained with an anti-cTn-1 antibody or an anti-SMα-actin antibody, and an anti-human mitochondria antibody.

As illustrated in FIG. 17, in the case where the adipose-derived stem cells having taken up the statin-included nanoparticles were administered to the myocardial infarction model mouse at $5 \times 10^4$ cells/mouse, staining of a fiberized part of the cardiac muscle tissue with the anti-cTn-1 antibody (arrow part) was observed, and the expression of the myocardial cell was observed. Moreover, staining with an hMtCd antibody was observed (arrow part), that is, it was revealed that administered human-adipose tissue-derived stem cells remain in the cardiac muscle tissue. Moreover, when these images were superimposed each other, areas where the stained areas overlap each other (arrow part) were observed. This suggests that the administered Adipose derived Stem Cell differentiated into a cardiac muscle. Note that staining with the SMα-actin antibody was also observed, but stained area stained with the SMα-actin antibody and stained area stained with the hMtCd antibody hardly overlapped each other.

These results suggest that in the case where the adipose-derived stem cells having taken up the statin-included nanoparticles were administered at a volume of $5 \times 10^4$ cells/mouse, accumulation and remaining of the administered cells in the ischemic myocardium tissue and also the differentiation of the cells into, in particular, myocardial cells occurred.

Next, accumulation effect of bone-marrow-derived endothelial progenitor cells (EPCs) on an infract part due to statin released from the adipose-derived stem cells having taken up the statin-included nanoparticles was studied. It is known that each EPC is one cell fractionation of blood corpuscle hematopoietic stem cells which are present in the bone marrow and that the EPCs differentiate into endothelial cells and/or myocardial cells included in a capillary vessel. Moreover, it is known that the EPC is a receptor of angiopoietin-1 which is one of vascular stabilizing factors, and that the EPCs are abundantly contained in a positive cell of Tie2 identified as a marker of an endothelial system cell. Thus, a Tie2/lacZ transgenic mouse in which a Tie2 positive cell is identifiable through immunostaining of β-galactosidase (β-gal) by gene recombination was used as a donner, and bone marrow monocytic cells were extracted from the bone marrow of the mouse.

The Tie2/lacZ transgenic mouse can be prepared by a general method. Specifically, a recombinant gene vector obtained by combining a lacZ gene in a mouse Tie2 promoter/enhancer was prepared, and then, from the recombinant gene vector amplified in bacteria, a mouse Tie2/lacZ gene expression vector was separated and purified and was microinjected in a mouse zygote, thereby preparing the Tie2/lacZ transgenic mouse. Moreover, the bone marrow monocytic cells were extracted as follows. First, the mouse was sacrificed, and then thighbones, lower leg bones, a backbone, and an ilium were separated, finely cut, and put in a mortar, and 20 mL 5 mM EDTA/PBS at a room temperature were added to the mortar, and the bone pieces were tapped with a pestle, thereby preparing a cell suspension. The cell suspension was collected into a new 50-mL tube through a cell strainer (40 µm, BD), and each 10 ml of the collected cell solution was gently superposed in a corresponding one of two 15-mL tubes containing 4 mL Histopaque 1083 (Sigma, 10831) at a room temperature without mixing. Then, centrifugation of these tubes was performed at a room temperature and at 800 g×20 min (without break), and after the centrifugation, only a mononuclear leukocyte cell layer was collected with a 2.5-mL syringe with a 18-G needle and was transferred into a new 15-mL tube, and cooled 5 mM EDTA/PBS was added to obtain a solution of 14 mL. Then, centrifugation at 200 g×10 min (with break) was performed, and supernatant was abandoned. Then, 1 mL cooled 5 mM EDTA/PBS suspended and diluted the cell to obtain a suspension of 14 mL, and then centrifugation at 200 g×10 min was performed, and supernatant was abandoned to prepare a bone marrow mononuclear cell pellet, which was used in a bone marrow transplantation experiment described below.

As the bone marrow transplantation, first, a 6 to 8-week-old male BALB/c nude mouse was irradiated with an X ray (twice at 5 Gy) to disrupt all bone marrow cells to obtain a mouse as a recipient mouse, and the bone marrow monocytic cells of the donor mouse prepared as described above were transplanted to the recipient mouse. Four weeks after the transplantation, in the recipient mouse, ischemia was induced (anterior descending coronary artery ligation model) in a manner similar to the above-described test, and three days after the induction, statin-capsulated PLA nanoparticles were administered to the caudal vein of the mouse. Note that the number of administered adipose-derived stem cells was $1 \times 10^4$ cells/mouse. An autopsy was performed on the mouse 25 days after the administration to prepare cut pieces of an infract part of the heart in a general method. Then, the cut pieces were immunostained with the anti-cTn-1 antibody, the anti-SMa actin antibody or the FITC-isolectin B4, an anti-β-gal antibody of the rabbit-derived IgG, and an Alexa 594 goat-derived anti-rabbit IgG antibody as a secondary antibody. The results are shown in FIG. 18.

Figure 18:
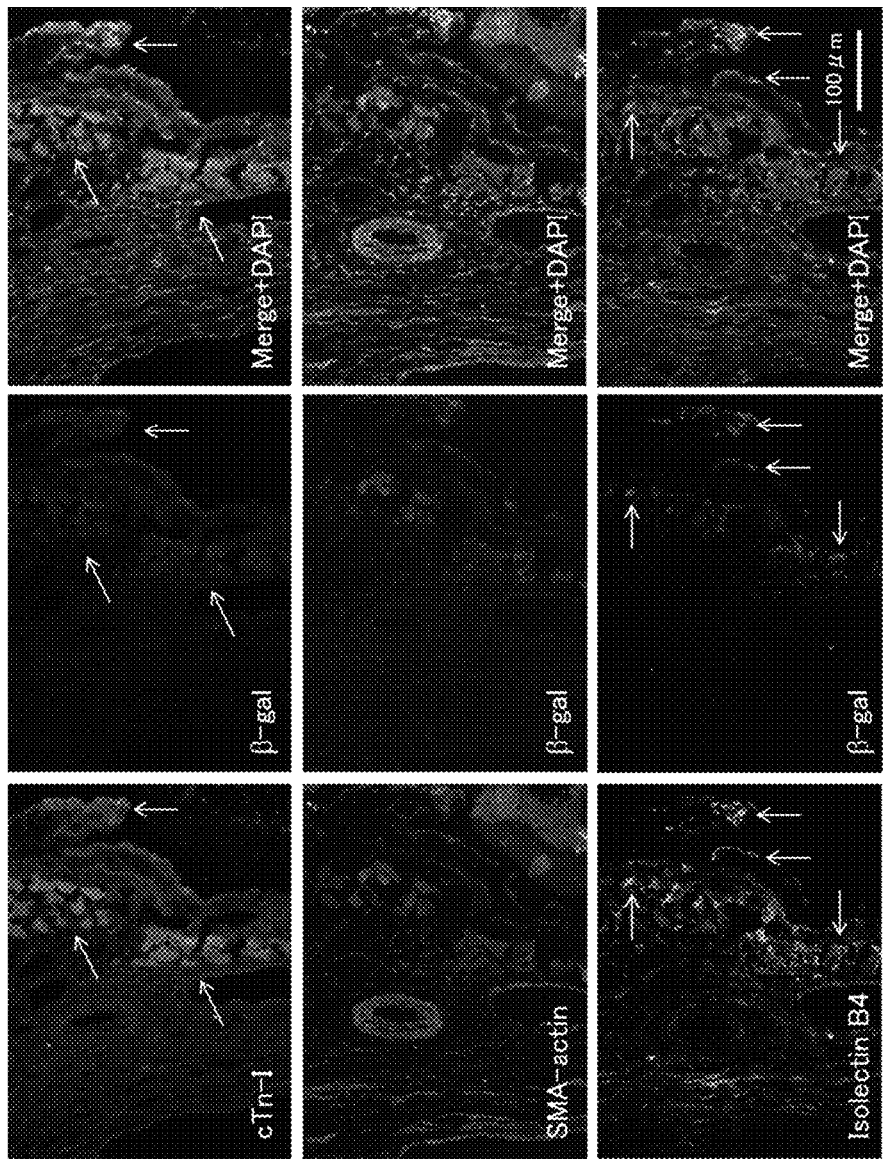
FIG. 18 shows photographs of cut pieces of an infarct part of the heart of a myocardial infarction mouse which has received bone marrow transplantation from a Tie2/lacZ transgenic mouse and which has administered with adipose-derived stem cells which have taken up statin-included nanoparticles, the cut pieces being immunostained with an anti-cTn-1 antibody, an anti-SMα actin antibody or isolectin B4, and an anti-β-galactosidase (β-gal) antibody.

As shown in FIG. 18, when the anti-cTn-1 antibody, the anti-SMα-actin antibody, and the FITC-isolectin B4 were used, the myocardial cell and the smooth muscle cell in the ischemic myocardium tissue were stained in a manner similar to the above results. Moreover, also when the β-gal antibody was used, stained areas in the ischemic myocardium tissue were observed. That is, it was observed that the EPCs from the bone marrow accumulated in the ischemic myocardium tissue. Moreover, when an image of the cut pieces stained with the anti-cTn-1 antibody or the FITC-isolectin B4 and an image of the cut pieces stained with the anti-β-gal antibody were superimposed on each other, stained areas of the images overlapped each other (arrow parts). This suggests that the EPCs accumulated from the bone marrow differentiated into myocardial cells. On the other hand, when an image of the cut piece stained with the anti-SMa actin antibody and an image of the cut piece stained with the β-gal antibody were superimposed on each other, almost no stained areas of the images overlapped each other.

These results suggest that when the adipose-derived stem cells having taken up the statin-included nanoparticles are administered to the myocardial infarction mouse, the adipose-derived stem cells accumulated at an ischemic injury cardiac muscle part release statin, so that the EPCs accumulate at the ischemic injury cardiac muscle part, the accumulated EPCs promote neovascularization, and differentiate into myocardial cells to promote treatment of the ischemic injury part.

Thus, the statin-included nanoparticles according to the present invention can enhance the functions, such as the migratory property, the proliferation characteristic, and the productivity of the neovascularization factor, and the like, of stem cells, and the stem cells with enhanced functions accumulate and proliferate at an infract part and release neovascularization factors, thereby promoting the neovascularization of the infraction part. Moreover, the accumulated and proliferating stem cells differentiate into cardiac muscle to promote regeneration of the cardiac muscle. Consequently, excellent therapeutic effects on the ischemic heart diseases such as a myocardial infarction are exhibited. Moreover, the stem cells are capable of gradually releasing statin which the stem cells have taken up, which offers various effects, such as neovascularization effects of the statin itself, which are typical of the statin. Thus, the stem cells are useful for the treatment of various diseases such as an ischemic heart disease. Moreover, statin released from the stem cells accumulated at a diseased part can facilitate accumulation of stem cells and/or bone marrow-derived endothelial progenitor cells (EPCs) in a body. As a result, for example, in the case of the ischemic heart disease, regeneration of the cardiac muscle at an infarction part can be further promoted. When a compound such as statin is simply intravenously administered, the compound is transported to a diseased part along with a bloodstream, but in the case of the ischemic heart disease such as a myocardial infarction, the bloodstream is inhibited, and therefore, it is difficult to normally transport the compound to the diseased part. However, in the case of the present invention, statin is incorporated into and transported by stem cells having an enhanced migratory property, and therefore, the compound can arrive at the diseased part even when the bloodstream is inhibited. That is, a good drug delivery system can be obtained, thereby enabling a reduction in the number of cells to be administered. Due to the actions described above, the present invention achieves extremely high effect on the treatment of ischemic heart diseases such as a myocardial infarction.

The invention claimed is:

1. A stem cell with an enhanced function, the stem cell comprising a statin-included nanoparticle for enhancing a function of the stem cell, the statin-included nanoparticle preparation comprising: a statin-included nanoparticle obtained by including statin in a nanoparticle comprising a bioabsorbable polymer, wherein the nanoparticle has a number average particle diameter of less than 1000 nm, wherein the function of the stem cell which is enhanced is at least one selected from the group consisting of a migratory capacity, a proliferation capacity, and a productivity of a neovascularization factor.

2. The stem cell according to claim 1, wherein the stem cell is an adipose-derived stem cell.

3. The stem cell according to claim 2, wherein the stem cell is a stem cell for treatment of an ischemic heart disease.

4. A cell preparation for intravenous administration, the cell preparation comprising the stem cell according to claim 1.

5. A method for manufacturing a stem cell with an enhanced function, the method comprising a step of treating a stem cell with the statin-included nanoparticle according to claim 1.

6. The method according to claim 5, wherein in the step of treating a stem cell with the statin-included nanoparticle, the statin-included nanoparticle is added to a medium for incubation of the stem cell to achieve a concentration of 20 µg/mL to 100 µg/mL.

7. The method according to claim 5, wherein in the step of treating a stem cell with the statin-included nanoparticle, time of the treating with the statin-included nanoparticle is 30 minutes to 2 hours.

8. The method according to claim 5, wherein the stem cell is an adipose-derived stem cell.

9. The method according to claim 5, wherein the stem cell is a stem cell for treatment of an ischemic heart disease.

* * * * *

UNITED STATES PATENT AND TRADEMARK OFFICE
CERTIFICATE OF CORRECTION

PATENT NO. : 10,278,926 B2
APPLICATION NO. : 15/525281
DATED : May 7, 2019
INVENTOR(S) : Masaaki Ii Page 1 of 1

It is certified that error appears in the above-identified patent and that said Letters Patent is hereby corrected as shown below:

On the Title Page

Item (22), under PCT Filed:, change "Nov. 11, 2015" to --Nov. 6, 2015--.

In the Specification

In Column 18, Line 56, change "anti-SMa" to --anti-SMα--.

In Column 20, Line 19, change "anti-SMa" to --anti-SMα--.

In Column 20, Line 39, change "anti-SMa" to --anti-SMα--.

Signed and Sealed this
Twenty-ninth Day of October, 2019

Andrei Iancu
*Director of the United States Patent and Trademark Office*

```
                        SEQUENCE LISTING

<160> NUMBER OF SEQ ID NOS: 6

<210> SEQ ID NO 1
<211> LENGTH: 18
<212> TYPE: DNA
<213> ORGANISM: Artificial Sequence
<220> FEATURE:
<223> OTHER INFORMATION: VEGF-A forward primer

<400> SEQUENCE: 1
ttactctcac ctgcttct                                                    18

<210> SEQ ID NO 2
<211> LENGTH: 18
<212> TYPE: DNA
<213> ORGANISM: Artificial Sequence
<220> FEATURE:
<223> OTHER INFORMATION: VEGF-A reverse primer

<400> SEQUENCE: 2
ctgcttcttc caacaatg                                                    18

<210> SEQ ID NO 3
<211> LENGTH: 19
<212> TYPE: DNA
<213> ORGANISM: Artificial Sequence
<220> FEATURE:
<223> OTHER INFORMATION: VEGF-C forward primer

<400> SEQUENCE: 3
tcaaggacag aagagacta                                                   19

<210> SEQ ID NO 4
<211> LENGTH: 19
<212> TYPE: DNA
<213> ORGANISM: Artificial Sequence
<220> FEATURE:
<223> OTHER INFORMATION: VEGF-C reverse primer

<400> SEQUENCE: 4
ccacatctat acacacctc                                                   19

<210> SEQ ID NO 5
<211> LENGTH: 19
<212> TYPE: DNA
<213> ORGANISM: Artificial Sequence
<220> FEATURE:
<223> OTHER INFORMATION: FGF-2 forward primer

<400> SEQUENCE: 5
ttcttccaat gtctgctaa                                                   19
```

```
<210> SEQ ID NO 6
<211> LENGTH: 20
<212> TYPE: DNA
<213> ORGANISM: Artificial Sequence
<220> FEATURE:
<223> OTHER INFORMATION: FGF-2 reverse primer

<400> SEQUENCE: 6
gaccaattat ccaaactgag                                                    20
```